US010835036B2

(12) United States Patent
Kim et al.

(10) Patent No.: US 10,835,036 B2
(45) Date of Patent: Nov. 17, 2020

(54) BATHROOM MANAGEMENT APPARATUS

(71) Applicant: LG ELECTRONICS INC., Seoul (KR)

(72) Inventors: Jeongyun Kim, Seoul (KR); Daeyun Park, Seoul (KR); Jinhyeon Jeon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 79 days.

(21) Appl. No.: 15/914,100

(22) Filed: Mar. 7, 2018

(65) Prior Publication Data
US 2018/0255923 A1   Sep. 13, 2018

(30) Foreign Application Priority Data

Mar. 7, 2017  (KR) .................. 10-2017-0028631

(51) Int. Cl.
*A47B 47/00* (2006.01)
*F25D 11/00* (2006.01)
(Continued)

(52) U.S. Cl.
CPC .......... *A47B 47/0091* (2013.01); *A47B 55/00* (2013.01); *A47B 67/005* (2013.01);
(Continued)

(58) Field of Classification Search
CPC ...... F24F 3/16; F24F 3/022; F24F 1/02; F24F 2003/144; A47B 55/00; A47B 47/0091; A47B 67/02; A47B 67/005; A47B 81/00; A47B 95/008; A47B 96/20; A47B 2096/208; F25D 11/00; F25D 23/12; H02J 7/0042; H02J 7/0027; A61L 2/10;
(Continued)

(56) References Cited

U.S. PATENT DOCUMENTS 1,918,047 A * 7/1933 Marchand ............ A47B 67/005
362/129
1,990,756 A * 2/1935 Saaf ....................... A47B 57/20
108/64
(Continued)

FOREIGN PATENT DOCUMENTS

| CN | 1140580 A | 1/1997 |
| CN | 202665369 U | 1/2013 |
| CN | 103622611 A | 3/2014 |

OTHER PUBLICATIONS

Chinese Office Action dated Apr. 15, 2020 issued in Application 201810186467.8 with English translation.

*Primary Examiner* — Hiwot E Tefera
*Assistant Examiner* — Timothy M Ayres
(74) *Attorney, Agent, or Firm* — KED & Associates LLP

(57) ABSTRACT

A bathroom management apparatus includes: a cabinet having an front surface; at least one frame configured to be attached to the cabinet; and at least one function module including at least one of a towel care module, a sterilizing module, a secret box module, a refrigerating module, a charging module, and an air conditioning module configured to be installed in the at least one frame, wherein the at least one frame provides a first mounting space, a second mounting space provided beneath the first mounting space, and a third mounting space provided beneath the second mounting space.

8 Claims, 22 Drawing Sheets

(51) Int. Cl.

| | |
|---|---|
| *A47B 81/00* | (2006.01) |
| *A47B 55/00* | (2006.01) |
| *F24H 3/02* | (2006.01) |
| *A61L 2/26* | (2006.01) |
| *A47B 67/00* | (2006.01) |
| *A61L 2/10* | (2006.01) |
| *A47B 96/20* | (2006.01) |
| *A47B 95/00* | (2006.01) |
| *H02J 7/00* | (2006.01) |
| *F25D 23/12* | (2006.01) |

(52) U.S. Cl.
CPC .............. *A47B 81/00* (2013.01); *A61L 2/10* (2013.01); *A61L 2/26* (2013.01); *F24H 3/022* (2013.01); *F25D 11/00* (2013.01); *A47B 95/008* (2013.01); *A47B 96/20* (2013.01); *A47B 2096/208* (2013.01); *A61L 2202/11* (2013.01); *A61L 2202/14* (2013.01); *F25D 23/12* (2013.01); *H02J 7/0027* (2013.01); *H02J 7/0042* (2013.01)

(58) Field of Classification Search
CPC .... A61L 2/26; A61L 2202/11; A61L 2202/14; A47K 10/06
USPC ........... 312/108, 242, 245–248, 257.1–265.6
See application file for complete search history.

(56) References Cited

U.S. PATENT DOCUMENTS

| | | | | |
|---|---|---|---|---|
| 2,439,664 A * | 4/1948 | Marchand | ............ | E05D 5/0246 312/242 |
| 2,553,965 A * | 5/1951 | Gist | ............ | A47B 67/02 312/242 |
| 2,879,124 A * | 3/1959 | Maxfield | ............ | A47B 67/02 312/242 |
| 3,008,785 A * | 11/1961 | Gehrs | ............ | A47B 67/005 312/209 |
| 3,185,534 A * | 5/1965 | Peters, Jr. | ............ | A47K 5/02 312/209 |
| 3,301,622 A * | 1/1967 | Zlatko | ............ | A47B 47/04 312/245 |
| 3,306,689 A * | 2/1967 | Anson | ............ | B65D 25/00 312/199 |
| 3,436,137 A * | 4/1969 | Ranger | ............ | A47B 57/10 312/408 |
| 3,732,702 A * | 5/1973 | Desch | ............ | A47B 67/005 62/3.6 |
| 4,437,712 A * | 3/1984 | Wissinger | ............ | A47B 67/005 312/209 |
| 4,644,136 A * | 2/1987 | Watchman | ............ | A47K 10/06 219/385 |
| 4,701,594 A * | 10/1987 | Powell | ............ | A45D 20/16 219/203 |
| 4,753,496 A * | 6/1988 | Bussard | ............ | F24F 7/065 312/116 |
| 4,966,424 A * | 10/1990 | Schneider | ............ | F16B 12/38 312/265.6 |
| 5,063,283 A * | 11/1991 | Orazi | ............ | A47G 1/02 219/218 |
| 5,378,057 A * | 1/1995 | Bach | ............ | A47B 47/02 312/257.1 |
| 5,524,980 A * | 6/1996 | Carter | ............ | A47B 67/02 211/88.01 |
| 5,620,105 A | 4/1997 | Macek | | |
| 5,647,651 A * | 7/1997 | Kim | ............ | A47B 67/00 312/209 |
| 5,785,402 A * | 7/1998 | DeLorenzo | ............ | A47B 67/04 312/350 |
| 6,089,685 A * | 7/2000 | Ryan | ............ | A47B 67/04 312/291 |
| 6,096,264 A * | 8/2000 | Peifer | ............ | H02J 7/0027 206/351 |
| 6,525,298 B1 * | 2/2003 | Hunts | ............ | A47K 10/06 219/385 |
| 6,565,166 B1 * | 5/2003 | Bulk | ............ | A47B 47/04 312/223.6 |
| 6,640,581 B1 * | 11/2003 | Choi | ............ | A47B 81/00 62/180 |
| 7,083,110 B2 * | 8/2006 | Kim | ............ | E06B 7/10 237/46 |
| 7,334,414 B2 * | 2/2008 | Park | ............ | A47D 13/00 62/3.3 |
| 8,058,588 B2 * | 11/2011 | Gagas | ............ | A47J 36/2483 219/400 |
| 8,517,478 B2 * | 8/2013 | Diemel | ............ | A47B 67/02 312/227 |
| 9,013,071 B1 * | 4/2015 | Levi | ............ | A45D 44/02 191/12 R |
| 9,433,694 B1 * | 9/2016 | Hsu | ............ | A46B 17/065 |
| 9,644,834 B2 * | 5/2017 | Cano | ............ | F21V 33/0012 |
| 10,045,617 B2 * | 8/2018 | Lehndorf | ............ | A47B 67/02 |
| 10,485,341 B2 * | 11/2019 | Dash | ............ | A47B 31/02 |
| 2003/0042828 A1 * | 3/2003 | Bonin | ............ | A47B 67/02 312/245 |
| 2009/0015121 A1 * | 1/2009 | Sampson | ............ | A47B 67/02 312/242 |
| 2010/0224615 A1 * | 9/2010 | Gallo | ............ | A47K 10/06 219/385 |
| 2018/0110382 A1 * | 4/2018 | Jeon | ............ | A47B 67/02 |
| 2018/0156477 A1 * | 6/2018 | Jeon | ............ | F24F 13/0272 |
| 2018/0249826 A1 * | 9/2018 | Kim | ............ | A47B 47/0091 |
| 2018/0249827 A1 * | 9/2018 | Kim | ............ | A47B 47/0091 |
| 2018/0249830 A1 * | 9/2018 | Jeon | ............ | A47B 67/005 |
| 2018/0251932 A1 * | 9/2018 | Jeon | ............ | A47B 81/00 |
| 2018/0252419 A1 * | 9/2018 | Kim | ............ | F24F 3/16 |
| 2018/0255923 A1 * | 9/2018 | Kim | ............ | F25D 11/00 |
| 2018/0258579 A1 * | 9/2018 | Kim | ............ | A47B 47/042 |
| 2018/0259204 A1 * | 9/2018 | Jeon | ............ | F24F 5/0042 |

* cited by examiner

FIG. 21
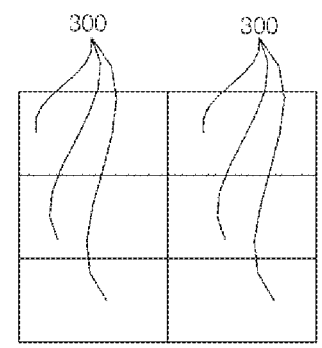
(a)
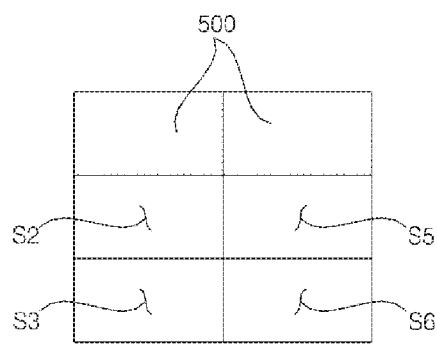
(b)
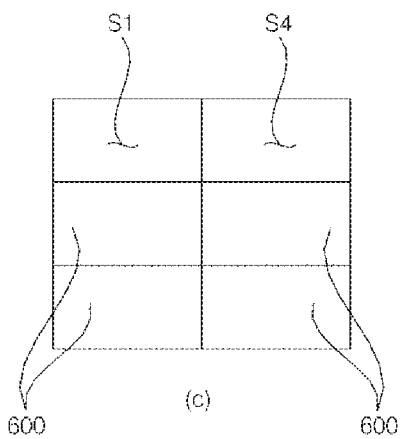
(c)
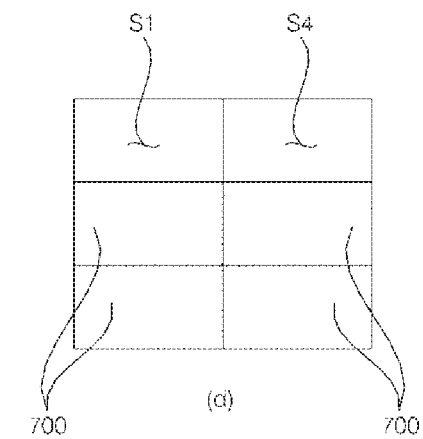
(d)
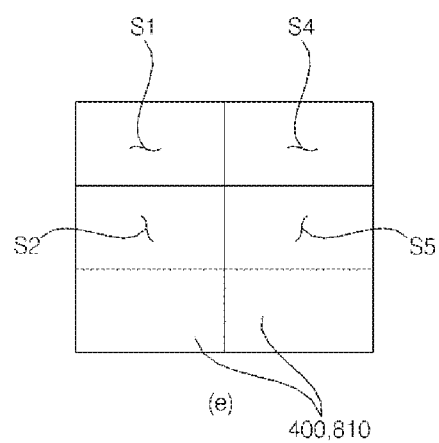
(e)

BATHROOM MANAGEMENT APPARATUS

CROSS-REFERENCE TO RELATED APPLICATION(S)

This application claims priority under 35 U.S.C. § 119 to Korean Application No. 10-2017-0028631 filed on Mar. 7, 2017, whose entire disclosure(s) is/are hereby incorporated by reference.

BACKGROUND

1. Field

A bathroom management apparatus which is installed at a bathroom to store various bath and toilet appliances including towels and to remove humidity in the bathroom is disclosed herein.

2. Background

A bathroom is a place that allows users to wash clothes, wash a face, wash hands, shower, and defecate, for example. Since the bathroom may be the most humid place, mold and bacteria may easily breed which may lead to unpleasant odors in the bathroom.

Some bathrooms may dry and deodorize using a ventilation fan. However, since an operation of the ventilation fan is not suitable or it is insufficient to dry the whole bathroom even while the ventilation fan is operated, pollution may occur due to breeding of mold and bacteria.

Accordingly, it is important to prevent mold and bacteria from forming in the bathroom by removing moisture from a bottom of the bathroom, and by drying wet bath and toilet appliances such as wet towels. Further, various facilities such as a washstand, a toilet, a mirror, a towel rack, and a toothbrush holder, for example, as well as a storage room for storing various bath and toilet appliances including towels may be installed in the bathroom. Meanwhile, a user may use electronic products such as hair dryers and shavers and apply make up in the bathroom.

If a bathroom management apparatus integrating a function of a toothbrush sterilizer, a function of a cosmetics refrigerator, and a charging function of the electronic products based on a function of the storage room and a dry function of the bathroom is developed, the space utility of the bathroom may be increased. Further, if a bathroom management apparatus independently including various function modules including a storage module having a function of the storage room, an air conditioning module having a drying function of the bathroom, a sterilizing module having a function of a toothbrush sterilizer, a refrigerating module having a function of a cosmetics refrigerator, and a charging module having a charging function of the electronic products is developed, the user may select necessary modules from the function modules to include the selected modules in the bath management apparatus.

In addition, an installation position of the function module may be freely changed by taking into consideration storage convenience and usability of the user. Since a toilet, a washstand, and a mirror may be installed in different positions in the bathroom according to users, the installation position of the function module may be freely changed according to an environment of the bathroom.

The above references are incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements wherein:

FIG. 21 illustrates an installation position of a function module by taking into consideration storage convenience and usability of a user.

DETAILED DESCRIPTION

Figure 1:
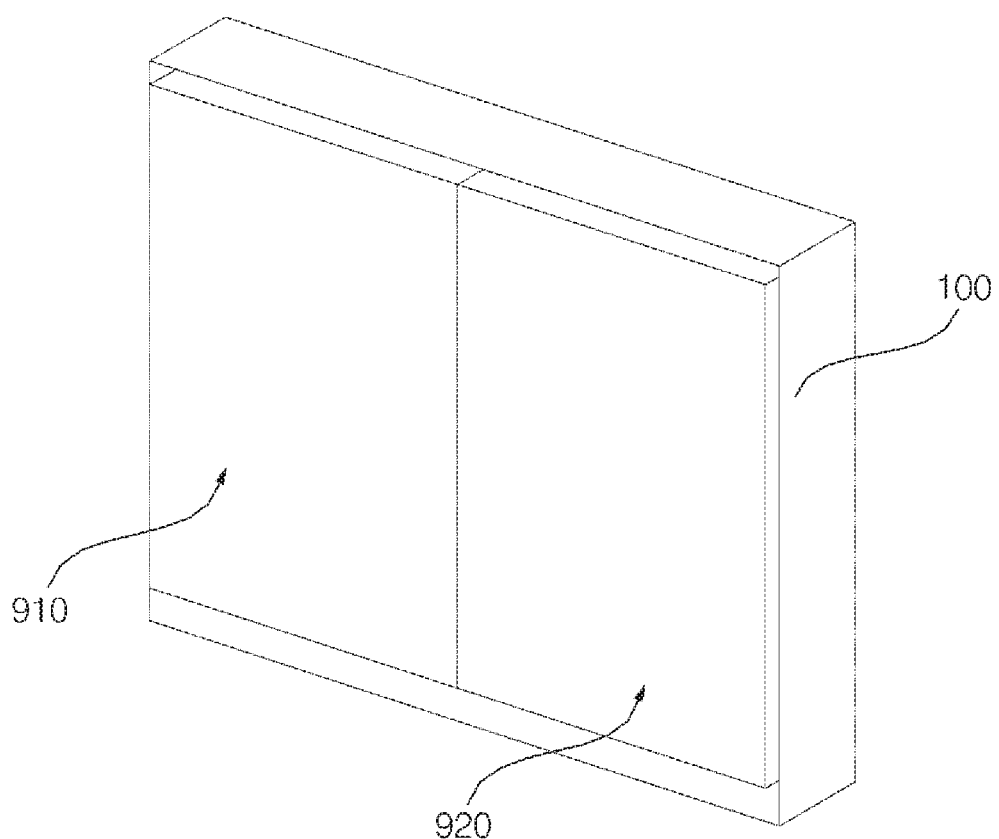
FIG. 1 is a combined perspective view showing a bathroom management apparatus according to an embodiment of the present disclosure.

Hereinafter, a bathroom management apparatus according to embodiments of the present disclosure will be described in detail with reference to the accompanying drawings. FIG. 1 is a combined perspective view showing a bathroom management apparatus according to an embodiment of the present disclosure, and FIG. 2 is an exploded perspective view showing a bathroom management apparatus according to the embodiment.

Figure 2:
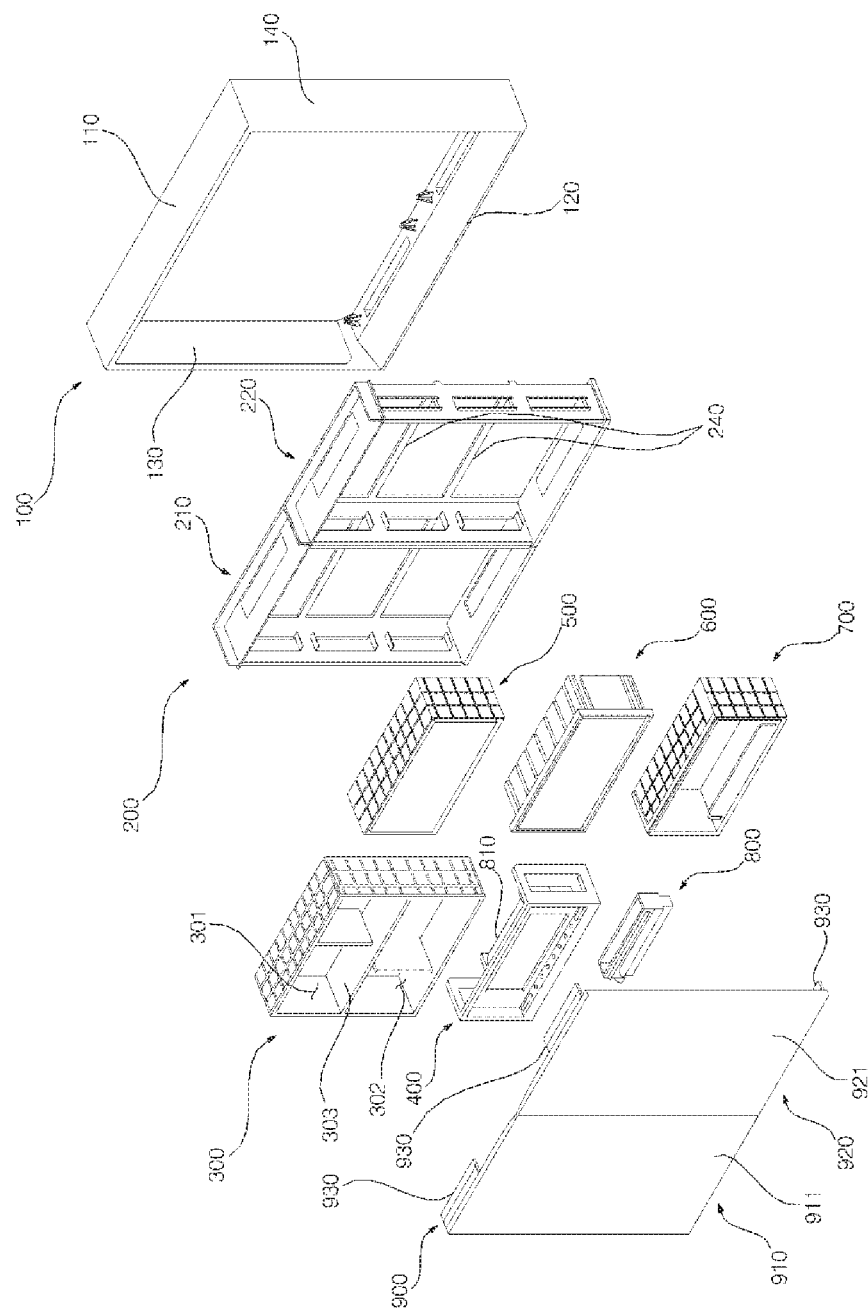
FIG. 2 is an exploded perspective view showing a bathroom management apparatus according to an embodiment.

Referring to FIG. 1 and FIG. 2, the bathroom management apparatus, or bathroom cabinet, may include a cabinet 100, a frame 200 installed inside the cabinet 100, a plurality of function modules 300, 400, 500, 600, 700, and 800, and a door 900 configured to open and close the cabinet 100. The cabinet 100 may have a hollow structure and may have a square shape of which a front surface and a rear surface are open. The cabinet 100 may form an upper external appearance, a lower external appearance, a first or left external appearance, and a second or right external appearance.

The cabinet 100 may include an upper panel 110 forming an upper side, a lower panel 120 forming a lower side, a first or left side panel 130 forming a left side, and a second or right side panel 140 forming a right side. The upper panel 110 may connect a top end of the left side panel 130 with a top end of the right side panel 140. The lower panel 120 may connect a bottom end of the left side panel 130 with a bottom end of the right side panel 140.

A left end of the upper panel 110 may be coupled with a top end of the left side panel 130 and a right end of the upper panel 110 may be coupled with a top end of the right side panel 130. Further, a left end of the lower panel 120 may be coupled with a lower end of the left side panel 130, and a right end of the lower panel 120 may be coupled with a bottom end of the right side panel 140.

The frame 200 may include frame bodies 210 and 220 having a square shape corresponding to the cabinet 100 of which a front surface and a rear surface are open, and back brackets 240 provided behind the frame bodies 201 and 220 to be coupled with rear surfaces of the frame bodies 210 and 220. The frame bodies 210 and 220 may reinforce stiffness of the cabinet 100. The bracket 240 may be thicker than the frame bodies 210 and 220 to reinforce the stiffness of the frame bodies 210 and 220.

The frame bodies 210 and 220 may provide a space therein in which the function modules 300, 400, 500, 600, 700, and 800 may be installed. The function modules 300, 400, 500, 600, 700, and 800 may include a towel care module 300, a sterilizing module 400, a secret box module 500, a refrigerating module 600, a charging module 700, and a blower out or exhaust module 800. The towel care module 300, the sterilizing module 400, the secret box module 500, the refrigerating module 600, the charging module 700, and the exhaust module 800 may be independently provided and installed inside the frame bodies 210 and 220 in a module unit. Ribs may protrude from upward, downward, left, and right sides of the function modules 300, 400, 500, 600, 700, and 800, respectively. The ribs protrude from left and right sides of the function modules 300, 400, 500, 600, 700, and 800 may be supported by an inner rib 215 to be described herein protruding in the frame bodies 210 and 220.

The towel care module 300 may include a function division plate 303. The function division plate 303 may vertically divide an inner space of the towel care module 300. The towel care module 300 may include a first storage space 301 for storing towels at a top side of the function division plate 303 and may further include a second storage space 302 for storing the towels at a bottom side of the function division plate 303 and drying and warming the stored towels. The towel care module 300 may include a first independent towel care module having only the first storage space 301 without the function division plate 303 and a second independent towel care module having only the second storage space 302.

The sterilizing module 400 may be used as a toothbrush sterilizer. The sterilizing module 400 may be configured to store toothbrushes, and may include a lamp for irradiating an ultra violet ray to the toothbrushes. The exhaust module 800 may be installed at a bottom side of the sterilizing module 400. An air conditioning module 810 including a blower to suck and blow air to the exhaust module 800 and a heater to heat the air blown from the blower may be installed at a rear portion of the sterilizing module 400 corresponding to a top side of the exhaust module 800 so that the sterilizing module 400 and the air conditioning module 810 may be integrally formed. The exhaust module 800 may exhaust the air blown from the blower into an inside of the bathroom.

The secret box module 500 may be used to store objects to prohibit children and customers from observing or touching the objects. The refrigerating module 600 may be used to refrigerate medicines and cosmetics. The refrigerating module 600 may be installed at a thermoelectric module, which may supply cold air into the refrigerating module 600 and may emit warm air to an outside of the refrigerating module 600.

The charging module 700 may be used to charge electronic devices such as a hair dryer and an electric shaver, for example. The charging module 700 may include a holder to hold the hair dryer and a receptacle to accept a power plug of the electronic device or a power plug of a charger for charging the electronic device.

Two frame bodies 210 and 220 may be provided and may include a first frame body 210 and a second frame body 220 provided adjacent to the first frame body 210. The first frame body 210 and the second frame body 220 may have the same structure. The towel care module 300, the sterilizing module 400, the secret box module 500, the refrigerating module 600, the charging module 700, and the exhaust module 800 may be selected and installed in any combination or duplication according to a need of a consumer. For example, only a plurality of towel care modules 300 may be installed, and two towel care modules 300 and one refrigerating module 600 may be installed in the frame bodies 210 and 220. According to the number of towel care modules 300, the sterilizing modules 400, the secret box modules 500, the refrigerating modules 600, and the charging modules 700 installed in the frame bodies 210 and 220, one or more frame bodies 210 and 220 may be provided.

The door 900 may form a front external appearance of the bathroom management apparatus. The door 900 may open/close an open surface of the cabinet 100. The same number of doors 900 may be provided by the corresponding number of the frame bodies 210 and 220. In an embodiment, since the two frame bodies 210 and 220 are provided, two doors 900 may be provided and may include a first door 910 and a second door 920. The first door 910 may be provided at a forward portion of the first frame body 210 and may open a left side of an open front surface of the cabinet 100, and the second door 920 may be provided at a forward portion of the second frame body 220 and may open a right side of an open front surface of the cabinet 100.

Mirrors 911 and 921 may be provided at front surfaces of the first door 910 and the second door 920, respectively. The mirrors 911 and 921 may be used instead of a mirror inside the bathroom. The mirrors 911 and 921 may include a first mirror 911 provided at a front surface of the first door 910 and a second mirror 921 provided at a front surface of the second door 920.

A hinge 930 may be installed at a rear surface of the door 900. The hinge 930 may include a first hinge member of which one end is coupled with a rear surface of the door and a second hinge member of which one end is rotatably coupled with an opposite end of the first hinge member and an opposite end is rotatably coupled with the frame bodies 210 and 220. The hinges 930 may be installed at a top side and a lower side of a rear surface of the first door 910, respectively, and may be installed at a top side and a bottom side of a rear side of the second door 910.

Figure 3:
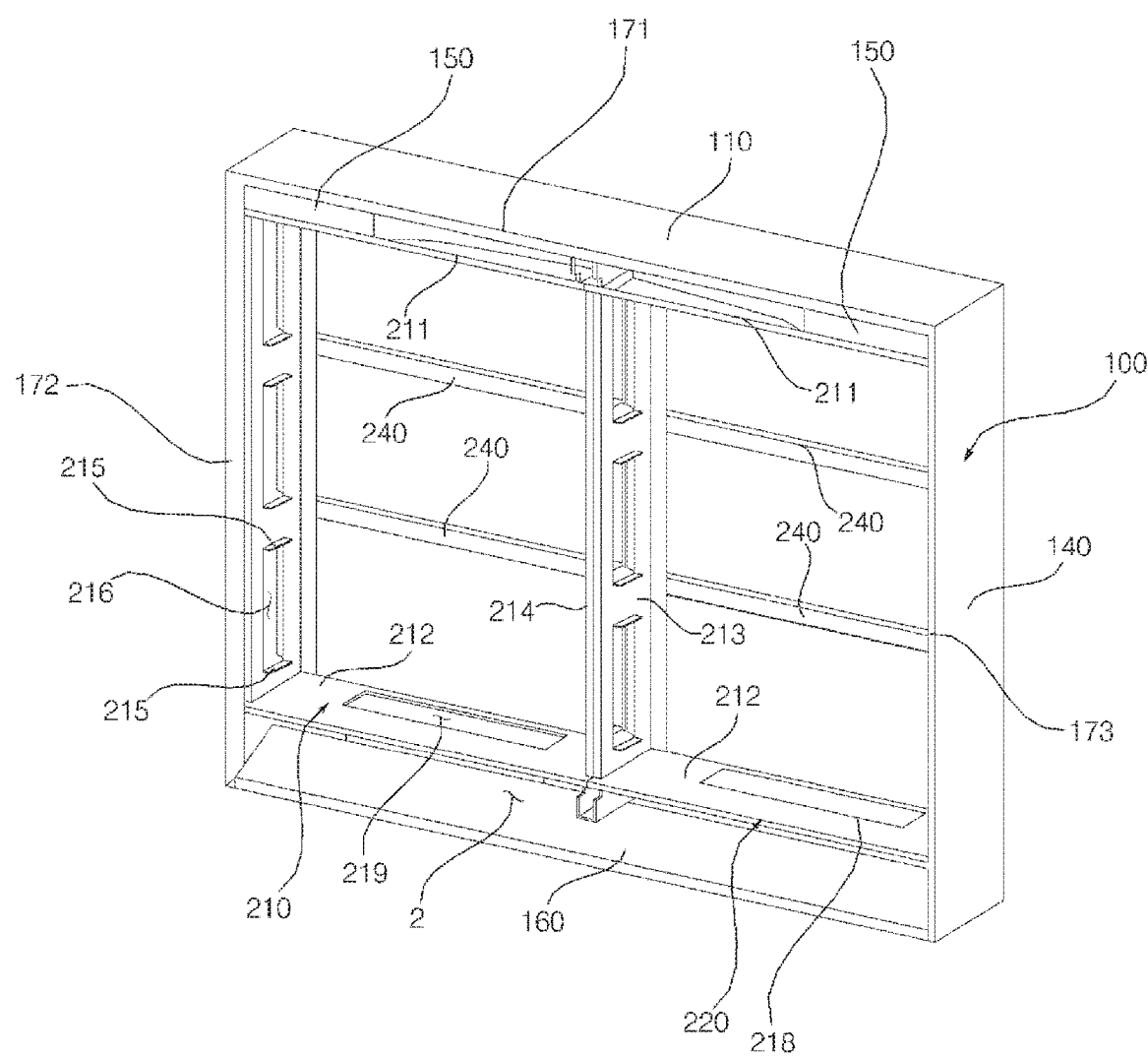
FIG. 3 illustrates a coupled state between the cabinet and the frame shown in FIG. 3.
Figure 4:
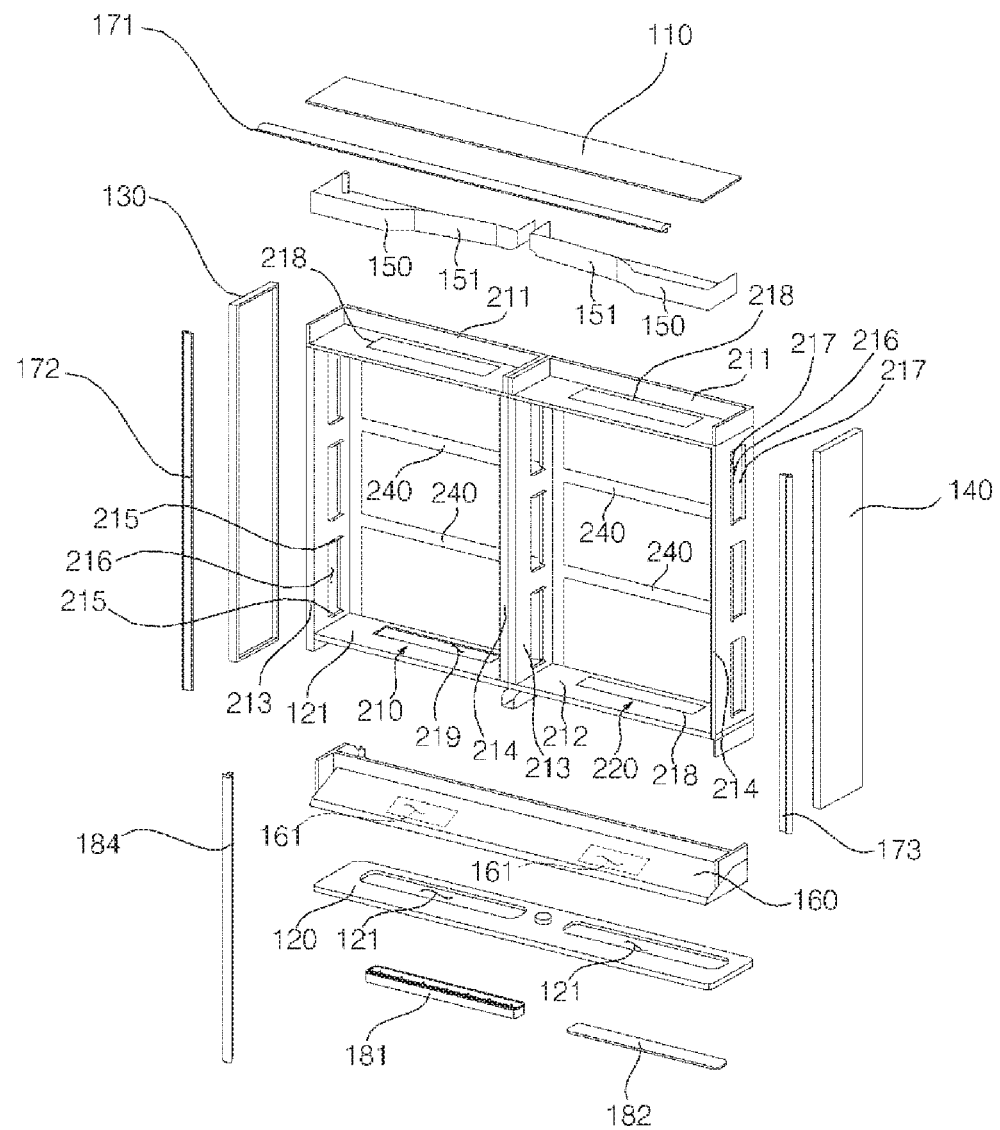
FIG. 4 is an exploded perspective view of FIG. 3.

FIG. 3 is a view illustrating a coupled state between the cabinet and the frame shown in FIG. 3, and FIG. 4 is an exploded perspective view of FIG. 3. Referring to FIG. 3 and FIG. 4, top surfaces and bottom surfaces of frame bodies 210 and 220 may be spaced apart from the cabinet 100. That is, the top surfaces of the frame bodies 210 and 220 may be spaced apart from the upper panel 110 of the cabinet 100 downward, and the bottom surfaces of the frame bodies 210 and 220 may be spaced apart from the lower panel 110 of the cabinet 100 upward.

An upper cover 150 may be provided between the upper panel 110 of the cabinet 100 and the top surfaces of the frame bodies 210 and 220. The upper cover 150 may be inserted into the space between the upper panel 110 of the cabinet 100 and the top surfaces of the frame bodies 210 and 220 to be coupled with the upper panel 110 of the cabinet 100 and the top surfaces of the frame bodies 210 and 220.

When a door 900 is closed, the upper cover 150 may cover the space between the upper panel 110 of the cabinet 100 and the top surfaces of the frame bodies 210 and 220 such that a hinge 930 installed at a rear top side of the door 900 may not be viewed from a rear direction of the bathroom management apparatus through a space between the upper panel 110 and top surfaces of the frame bodies 210 and 220. When the door 900 is open, the upper cover 150 may prevent the bathroom wall from being viewed from the forward direction of the bathroom management apparatus through a space between the upper panel 110 and the top surface of the frame bodies 210 and 220.

The upper cover 150 may have a shape of which a top surface and a rear surface are open to include a bottom surface, a front surface, a left surface, and a right surface. A concave groove 151 configured to receive a hinge 930 when the door 900 is closed may be formed at the front surface of the upper cover 150 so that a space for receiving the hinge 930 may be formed between the upper panel 110 and the top surfaces of the frame bodies 210 and 220.

Further, a control panel 160 may be inserted between the lower panel 120 of the cabinet 100 and bottom surfaces of the frame bodies 210 and 220. The control panel 160 may be inserted between the lower panel 120 of the cabinet 100 and bottom surfaces of the frame bodies 210 and 220 to be coupled with the lower panel 120 of the cabinet 100 and the bottom surfaces of the frame bodies 210 and 220.

Remaining regions of the control panel 160 except for a top side coupled with the bottom surfaces of the frame bodies 210 and 220 may be spaced apart from the bottom surfaces of the frame bodies 210 and 220. Air exhausted from the exhaust module 800 may be moved toward a first air outlet 2 to be described herein through a space between bottom surfaces of the frame bodies 210 and 220 and a top side of the control panel 160. After the user showers, for example, the user may dry a user's body using air exhausted into the bathroom from the first air outlet 2.

A user interface as well as an input unit (or input) for controlling function modules 300, 400, 500, 600, 700, 800, and 810 may be installed at the control panel 160. The input may include at least one of a button and a touch screen, and the user may push or touch the input to operate or stop the function modules 300, 400, 500, 600, 700, 800, and 810. An installed region of the input of the control panel 160 may be exposed below of the door 900 when the door 900 is closed.

Meanwhile, the cabinet 100 may include decoration members 171, 172, and 173 coupled with a front end of the upper panel 110, a front end of the left side panel 130, and a front end of the right side panel 140, respectively. The decoration members 171, 172, and 173 may include a first decoration member 171 coupled with a front end of the upper panel 100, a second decoration member 172 coupled with a front end of the left side panel 130, and a third decoration member 173 coupled with a front end of the right side panel 140.

The decoration members 171, 172, and 173 may not be installed at a front end of the lower panel 120 but the front end of the lower panel 120 may be covered by a front end of the control panel 160. That is, the control panel 160 may act as a decoration member by covering the front end of the lower panel 120. The control panel 160 may be formed with the same color and material as the decoration members 171, 172, and 173. The frame bodies 210 and 220 may include an upper frame 211 forming an upper side, a lower frame 212 forming a lower side, and a left or first side frame 213 forming a left side, and a right or second side frame 214 forming a right side.

The upper frame 211 may connect a top end of the left side frame 213 with a top end of the right side frame 214. The lower frame 212 may connect a bottom end of the left side frame 213 with a bottom end of the right side frame 214.

A left end of the upper frame 211 may be coupled with a top end of the left side frame 213, and a right end of the upper frame 211 may be coupled with a top end of the right side frame 214. Further, a left end of the lower frame 212 may be coupled with a bottom end of the left side frame 213, and a right end of the lower frame 212 may be coupled with a bottom end of the right side frame 214.

The upper frame 211 and the lower frame 212 may have the same structure. The left side frame 213 and the right side frame 214 may have the same structure. Accordingly, the first frame body 210 and the second frame body 220 may be installed inside the cabinet 100 regardless of upper and lower sides and regardless of left and right sides.

The upper frame 211 may have a shape such that a top surface and a front surface are open and may include a bottom surface, a left surface, a right surface, and a rear surface. Further, the lower frame 212 may have an upside down shape of the upper frame 211 and may have a shape of which a bottom surface and a front surface are open. That is, the lower frame 212 may include a left surface, a right surface, and a rear surface.

First opening portions or slots 216 having a square shape may be formed in the left side frame 213 and the right side frame 214, respectively. The first opening portion 216 may form a path through which wires of the function modules 300, 400, 500, 600, 700, and 800 pass. The same number of the first opening portions 216 may be formed by the corresponding number of the function modules 300, 400, 500, 600, 700, and 800 installed inside the frame bodies 210 and 220.

Inner ribs 215 may be formed at inner sides of the left side frame 213 and the right side frame 214, respectively. The inner ribs 215 may protrude toward the interior of the frame bodies 210 and 220 from a top side and a bottom side of the first opening portion 216.

The inner rib 215 may guide insertion of the function modules 300, 400, 500, 600, 700, and 800 when the function modules 300, 400, 500, 600, 700, and 800 are individually inserted into the frame bodies 210 and 220. After the function modules 300, 400, 500, 600, 700, and 800 are inserted into the frame bodies 210 and 220, the inner rib 215 may support the function modules 300, 400, 500, 600, 700, and 800.

Outer ribs 217 may be formed at outer sides of the left side frame 213 and the right side frame 214, respectively. The outer ribs 217 may protrude to outer sides of the frame bodies 210 and 220 from a front side and a rear side of the first opening portion 216, respectively. The outer ribs 217 may be spaced apart from each other in forward and reward directions while interposing the first opening portion 216 therebetween to form a path through which wires of the function modules 300, 400, 500, 600, 700, and 800 pass after the wires of the function modules 300, 400, 500, 600, 700, and 800 pass through the first opening portion 216.

Cut lines 218 having a square shape may be formed at a bottom surface of the upper frame 211 and a top surface of the lower frame 212, respectively. The cut lines 218 may be formed by partially cutting a bottom surface of the upper frame 211 and a top surface of the lower frame 212 so that a worker may easily separate an inner region divided by the cut lines 218 from a bottom surface of the upper frame 211 an a top surface of the lower frame 212.

When the sterilizing module 400 is installed close to the upper frame, the worker may cut the cut line 218 formed at the upper frame 211 among the cut line 218 formed at the upper frame 211 and the cut line 218 formed at the lower frame 212 to separate an inner region of the upper frame 211 divided by the cut line 218. When the sterilizing module 400 is installed close to the lower frame, the worker may cut the cut line 218 formed at the lower frame 211 among the cut line 218 formed at the upper frame 211 and the cut line 218 formed at the lower frame 212 to separate an inner region of the lower frame 212 divided by the cut line 218.

The second slots 219 may be formed at the upper frame 211 and the lower frame 212 when the inner region divided by the cut line 218 is separated by the worker. Further, a third opening portion or slot 161 may be formed at a lower side of the second slot 219 in a lower side of the control panel 160. Further, a fourth opening portion or slot 121 may be formed at a lower side of the third opening portion 161 in a lower panel 120 of the cabinet 100.

A blower louver 181 may be installed at a region corresponding to the fourth slot 121 or a lower cover 182 may be installed in the top surface of the lower panel 120. When the fourth slot 121 is located under the sterilizing module 400, the blower louver 181 may be installed at a region corresponding to the fourth slot 121 in the lower panel 120. Otherwise, the lower cover 182 may be installed at a region corresponding to the fourth slot 121 in the lower panel 120 so that the fourth slot 121 is shielded by the lower cover 182.

Figure 12:
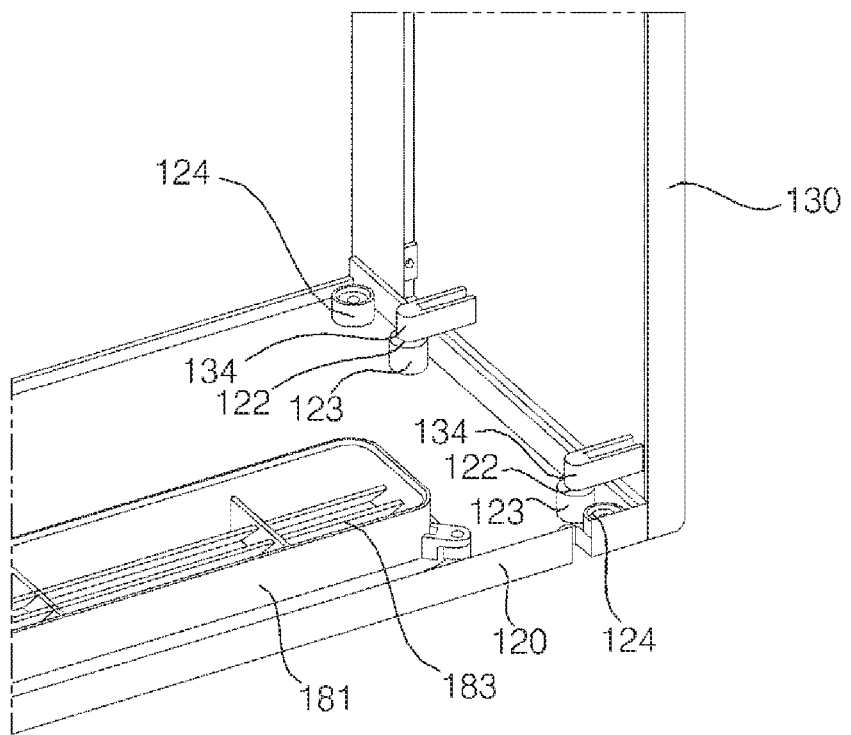
FIG. 12 is a rear perspective view illustrating a lower panel and a left side panel shown in FIG. 4.

As shown in FIG. 12, the blower louver 181 may include a discharge grill 183, and may be installed at a region corresponding to the fourth slot 121 in the lower panel 120 to guide air from the exhaust module 800 into the fourth slot 121. When the blower louver 181 is installed at a region corresponding to the fourth slot 121 in the lower panel 120, the fourth slot 121 may become the second air outlet 121. That is, in the cabinet 100, the first air outlet 2 may be spaced apart from a lower frame 212 being a bottom surface of the frame 200, and a second air outlet 121 may be formed at a bottom surface of the frame 200.

The exhaust module 800 may be located inside the control panel 160 between the lower panel 120 and the lower frame 212. Further, a top end of the exhaust module 800 may be inserted into the second slot 219 so that the exhaust module 800 sucks air blown from the blower, and a bottom end of the exhaust module 800 may be connected to the blower louver 181 through the third slot 161. Moreover, a front opening portion communicating with the first air outlet 2 may be formed at a front surface of the exhaust module 800.

Since the exhaust module 800 includes a motor and a fluid path switching vane rotated by a driving force of the motor, the fluid path switching vane may be rotated by the driving force of the motor to open the front opening portion and close a bottom end. Air sucked from an air conditioning module 810 may pass through the front opening portion and may be discharged into the bathroom through the first air outlet 2. When the front opening portion is closed and the bottom end is open, the air sucked from the blower may pass through the blower louver 181 and may be discharged into the bathroom through the second air outlet 121. That is, the exhaust module 800 may switch the air blown from the air conditioning module 810 to one of the first air outlet 2 and the second air outlet 121.

A user may control a rotation position of the fluid path switching vane of the exhaust module 800 by operating the input installed at the control panel 160 to discharge air into the bathroom through the first air outlet 2 or to discharge the air into the bathroom through the second air outlet 121. The air discharged into the bathroom through the first air outlet 2 may be used to dry the user's body. The air discharged into the bathroom through the second air outlet 121 may be used to dry an inside of the bathroom.

When a plurality of frame bodies 210 and 220 are provided, a center cover 184 may be further installed at front surfaces of adjacent side frames 214 and 213 of the plurality of frame bodies 210 and 220. That is, two frame bodies 210 and 220 may be provided, and center covers 184 may be installed at a front surface of the right side frame 214 of the first frame body 210 and a front surface of a left side frame 213 of the second frame body 220, respectively.

The center cover 184 may cover the right side frame 214 of the first frame body 210 and the left side frame 213 of the second frame body 220 in a forward direction. In addition, after the function modules 300, 400, 500, 600, and 700 are inserted into the frame bodies 210 and 220, the center cover 184 may protrude to both sides of the function modules 300, 400, 500, 600, and 700 to cover a module locking rib locked at a front surface of the both side frames 213 and 214 of the frame bodies 210 and 220.

Figure 5:
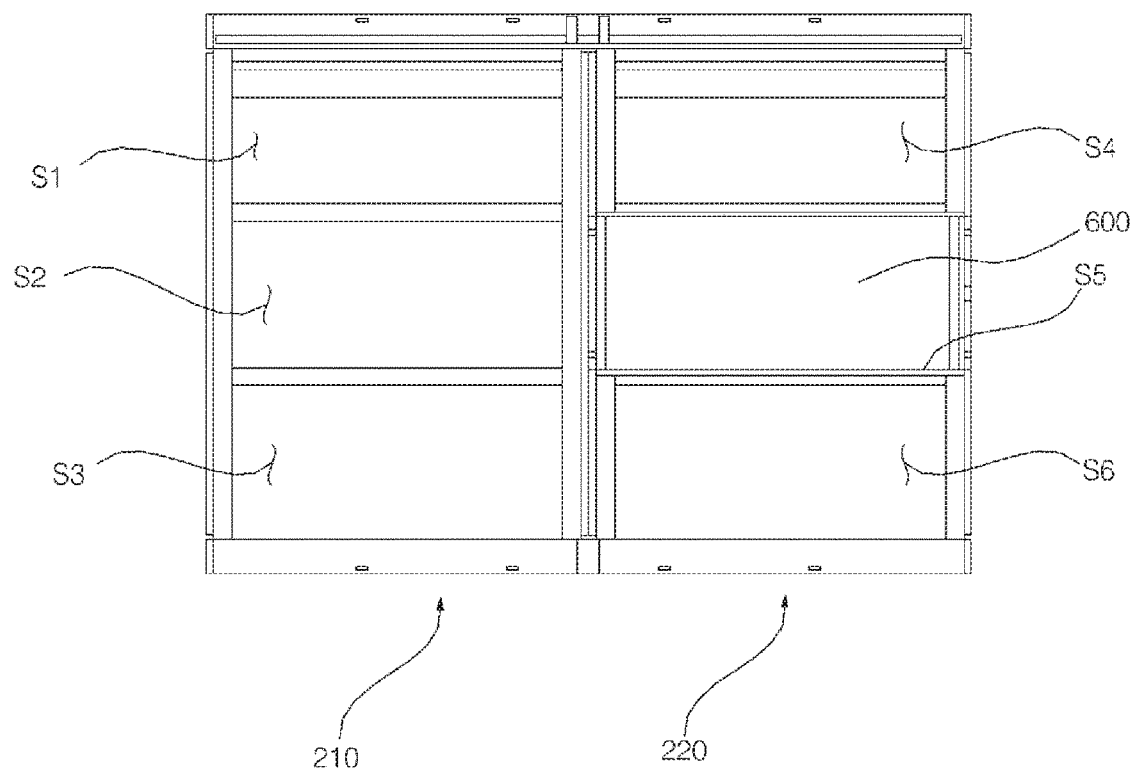
FIG. 5 is a front view illustrating an installed state of the function module inside a frame of a bathroom management apparatus according to an embodiment.
Figure 6:
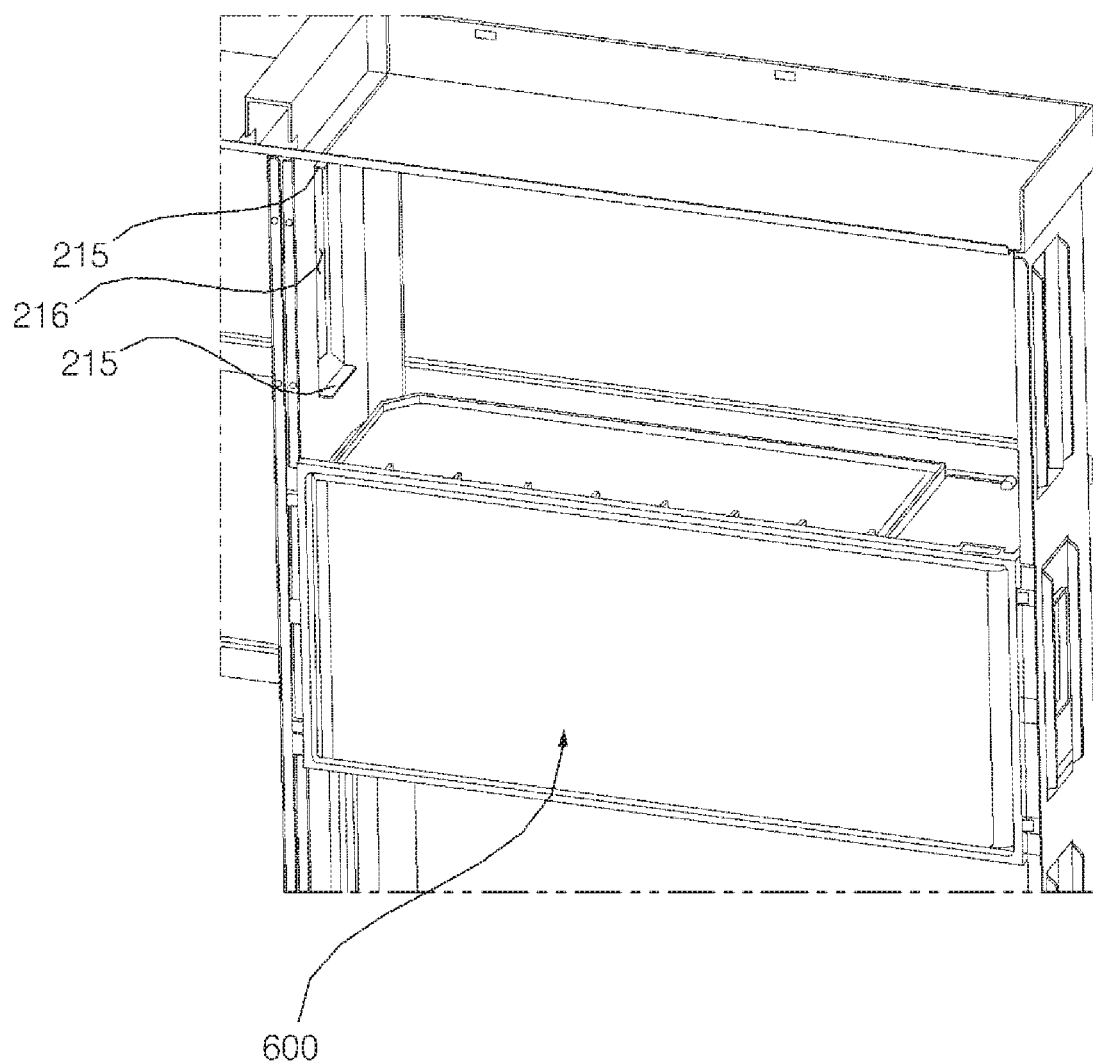
FIG. 6 is a perspective view illustrating an installed state of the function module inside a frame of a bathroom management apparatus according to an embodiment.
Figure 7:
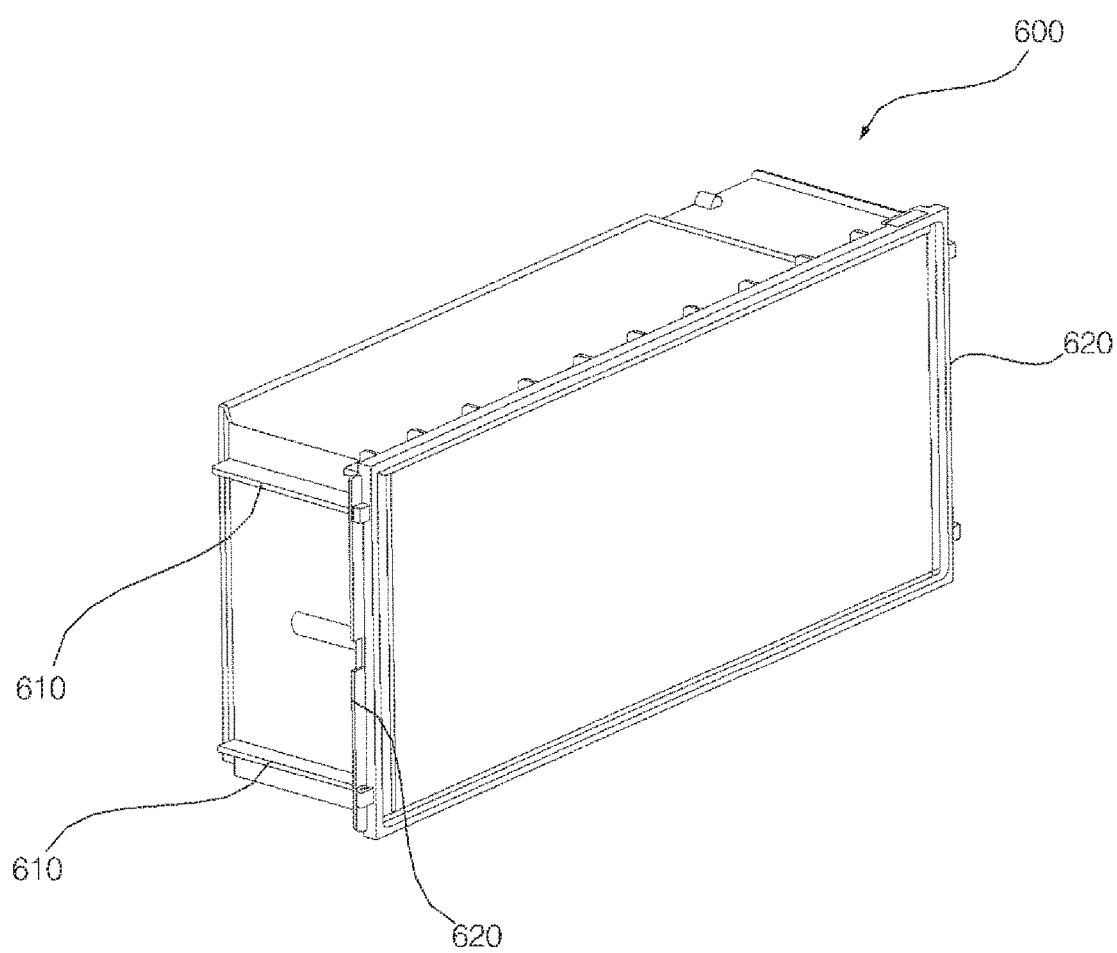
FIG. 7 is a perspective view illustrating the function module installed inside a frame of a bathroom management apparatus according to an embodiment.
Figure 8:
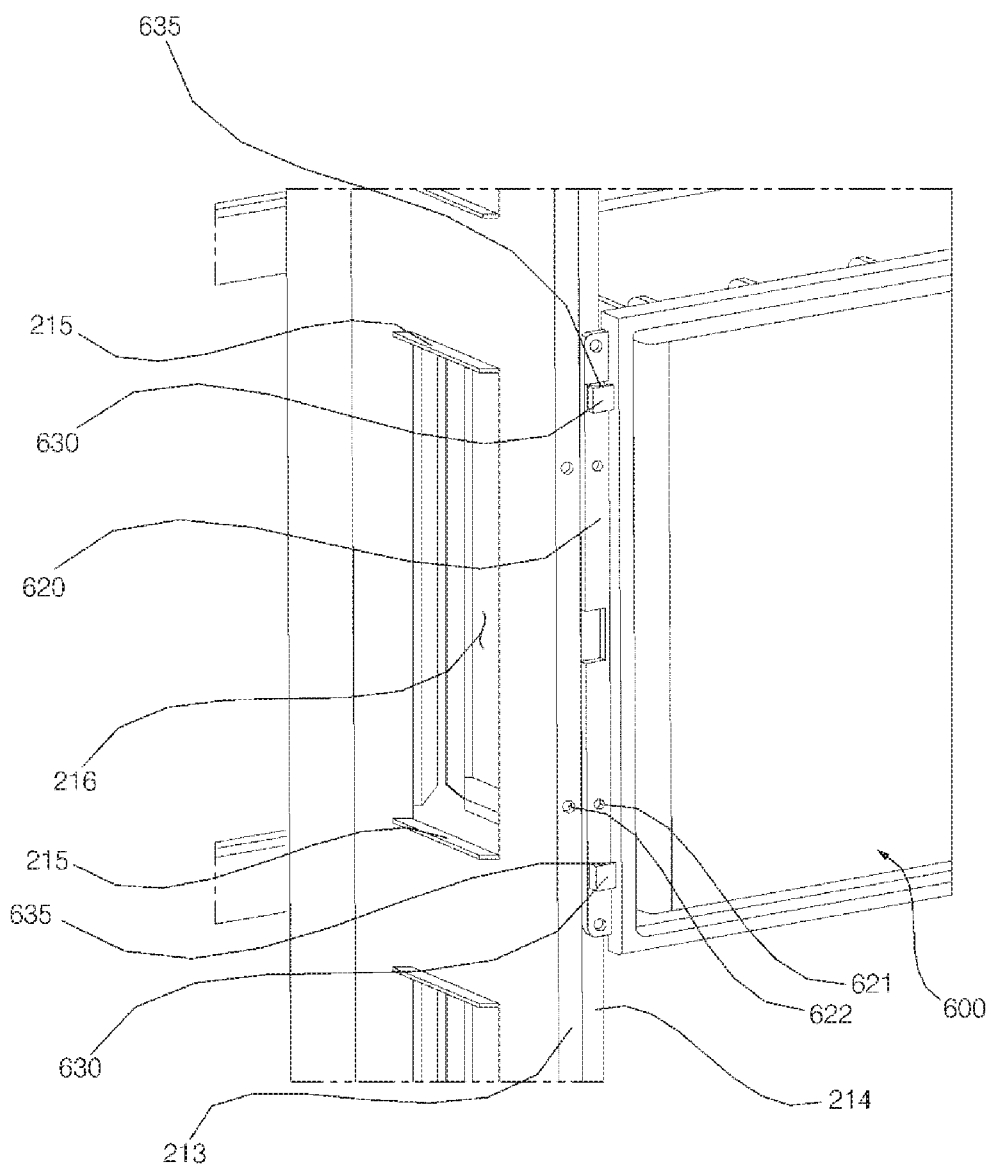
FIG. 8 is a partially enlarged view of FIG. 6.

Hereinafter, an operation of installing the function modules 300, 400, 500, 600, and 700 in the frame bodies 210 and 220 is described with reference to FIG. 5 to FIG. 8. FIG. 5 is a front view illustrating an installed state of the function module inside a frame of a bathroom management apparatus, FIG. 6 is a perspective view illustrating an installed state of the function module inside a frame of a bathroom management apparatus, FIG. 7 is a perspective view illustrating the function module installed inside a frame of a bathroom management apparatus, and FIG. 8 is a partially enlarged view of FIG. 6.

Referring to FIG. 2 and FIG. 5, the frame bodies 210 and 220 may provide mounting spaces S1, S2, S3, S4, S5, and S6 in which the function modules 300, 400, 500, 600, and 700 may be inserted and mounted at an inner side thereof. The mounting spaces S1, S2, S3, S4, S5, and S6 may include a first mounting space S1 located at the uppermost side of the first frame body 210, a second mounting space S2 located at a middle of the first frame body 210, a third mounting space S3 located at the lowermost side of the first frame body 210, a fourth mounting space S4 located at the uppermost side of the second frame body 220, a fifth mounting space S5 located at a middle of the second frame body 220, and a sixth mounting space S6 located at the lowermost side of the second frame body 220.

The first mounting space S1, the second mounting space S2, the third mounting space S3, the fourth mounting space S4, the fifth mounting space S5, and the sixth first mounting space S6 may have the same size. The second mounting space S2 may be located at a lower side of the first mounting space S1, the third mounting space S3 may be located at a lower side of the second mounting space S2, the fourth mounting space S4 may be located adjacent to the first mounting space S1, the fifth mounting space S5 may be located at a lower side of the fourth mounting space S4, and the sixth mounting space S6 may be located at a lower side of the fifth mounting space S5.

The fourth mounting space S4 may be located at one side of the first mounting space S1, the fifth mounting space S5 may be located at one side of the second mounting space S2, and the sixth mounting space S6 may be located at one side of the third mounting space S3. The first mounting space S1 and the fourth mounting space S4 may be located at the same height upward and downward. The second mounting space S2 and the fifth mounting space S5 may be located at the same height upward and downward. The third mounting space S3 and the sixth mounting space S6 may be located at the same height upward and downward. The first mounting space S1, the second mounting space S2, the third mounting space S3, the fourth mounting space S4, the fifth mounting space S5, and the sixth first mounting space S6 may have the same vertical length and may have different horizontal lengths.

The towel care module 300 may be inserted into and mounted in the first mounting space S1 and the second mounting space S2 being adjacent mounting spaces among the first mounting space S1, the second mounting space S2, and the third mounting space S3. In addition, the towel care module 300 may be inserted into and mounted in the fourth mounting space S4 and the fifth mounting space S5 or the fifth mounting space S5 and the sixth mounting space S6 being adjacent mounting spaces among the fourth mounting space S4, the fifth mounting space S5, and the sixth mounting space S6.

The sterilizing module 400, the secret box module 500, the refrigerating module 600, and the charging module 700 may be mounted at one of the first mounting space S1, the second mounting space S2, the third mounting space S3, the fourth mounting space S4, the fifth mounting space S5, and the sixth mounting space S6.

The towel care module 300 may be inserted into and mounted in the first mounting space S1 and the second mounting space S2. The sterilizing module 400 may be inserted and mounted in the third mounting space S3. The secret box module 500 may be inserted and mounted in the fourth mounting space S4. The refrigerating module 600 may be inserted and mounted in the fifth mounting space S5. The charging module 700 may be inserted and mounted in the sixth mounting space S6.

Since the towel care module 300 is configured by integrating the first towel care module and the second towel care module as one, the towel care module 300 may have a vertical length of double that of the sterilizing module 400, the secret box module 500, the refrigerating module 600, and the charging module 700 to be inserted into and mounted in the first mounting space S1 and the second mounting space S2. However, the first towel care module and the second towel care module may be separately provided, the first towel care module may be inserted into and mounted in one of the first mounting space S1 and the second mounting space S2, and the second towel care module may be inserted into and mounted in a remaining one. The towel care module 300, the sterilizing module 400, the secret box module 500, the refrigerating module 600, and the charging module 700 may have the same horizontal length.

Hereinafter, since the same configuration inserts and mounts the function modules 300, 400, 500, 600, and 700 into the frame 200, only the refrigerating module 600 of the function modules 300, 400, 500, 600, and 700 will be described as an example. Referring to FIG. 6 to FIG. 8, guide ribs 610 may be formed at both sides of the function module 600, respectively. Although FIG. 7 illustrates that the guide rib 610 is formed at a left side of the function module 600, the same guide rib 610 may be formed at the right side of the function module 600. When the function module 600 is inserted into the frame 200, the guide ribs 610 formed at the both sides of the function module 600 may be guided by the inner ribs 215 formed at the left side frame 213 and the right side frame 214, respectively to be inserted into the frame 200. After the function module 600 is inserted into the frame 200, the guide ribs 610 may be supported by the inner rib 215.

A pair of guide ribs 610 may be vertically spaced apart from each other on both sides of the function module 600. An upper guide rib 610 of a pair of guide ribs 610 formed at the left side of the function module 600 may be placed on a top side of the inner rib 215 protruding from a top side of the first opening portion 216 of the left side frame 213. A lower guide rib 610 of the pair of guide ribs 610 formed at the left side of the function module 600 may be placed on a top side of the inner rib 215 protruding from a bottom side of the first opening portion 216 of the left side frame 213.

An upper guide rib 610 of a pair of guide ribs 610 formed at the right side of the function module 600 may be placed on a top side of the inner rib 215 protruding from a top side of the first opening portion 216 of the right side frame 213. A lower guide rib 610 of the pair of guide ribs 610 formed at the right side of the function module 600 may be placed on a top side of the inner rib 215 protruding from a bottom side of the first opening portion 216 of the right side frame 213.

Module locking ribs 620 locking at front ends of the left side frame 213 and the right side frame 214 may be further formed at both sides of the function module 600. The module locking ribs 620 may be located in a forward direction of the guide ribs. The module locking ribs 620 may be formed at both sides of a front edge of the function module 60, respectively. The module locking ribs 620 may be locked with the left side frame 213 and the right side frame 214 with a screw, for example. The module locking rib 620 may include a locking hole 620 through which the screw may pass. Locking holes 622 may formed through front ends of the left side frame 213 and the right side frame 214, and the screw may be inserted into the locking hole 621 in the forward direction of the module locking rib 620 and then may be inserted into the locking hole 620 so that the function module 600 is locked with the frame 200.

The module locking rib 620 formed at a left side of the function module 600 may be locked with a front end of the left side frame 213. The module locking rib 620 formed at a right side of the function module 600 may be locked with a front end of the right side frame 214.

Figure 16:
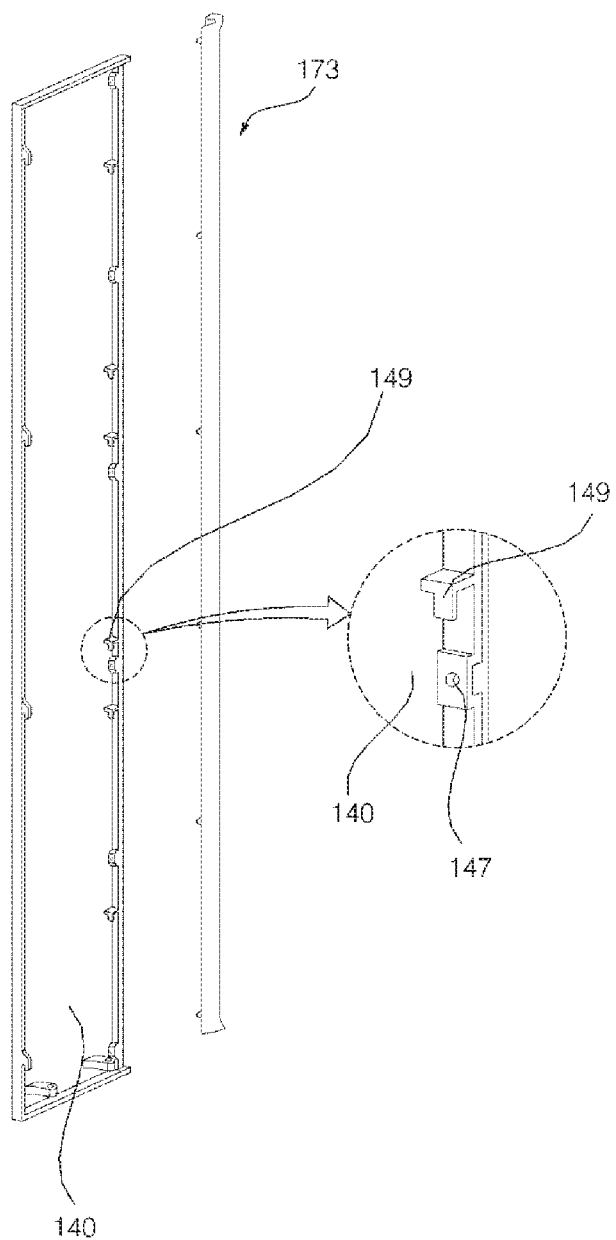
FIG. 16 is a right perspective view illustrating a right side panel and a decoration member shown in FIG. 4.

Further, the module locking rib 620 may include a first module locking protrusion 630 including a module locking groove 635. When the second module locking protrusion 149 shown in FIG. 16 is inserted and locked in the module locking groove 635, the first module locking protrusion 630 may lock the function module 600 in the cabinet 100. A detailed description thereof is described with reference to FIG. 16. After the function module 600 is mounted in the frame 200, the module locking rib 620 may be covered by the center cover 184.

Figure 9:
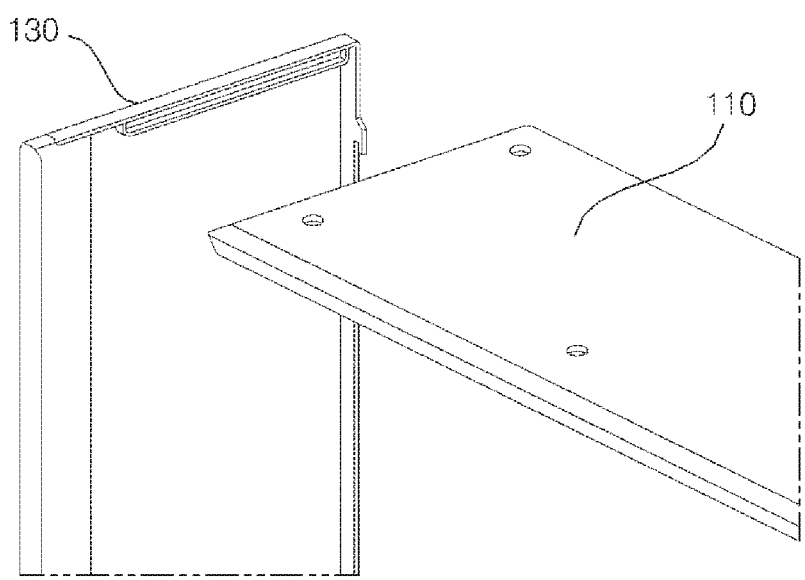
FIG. 9 is a right perspective view illustrating an upper panel and a left side panel shown in FIG. 4.
Figure 10:
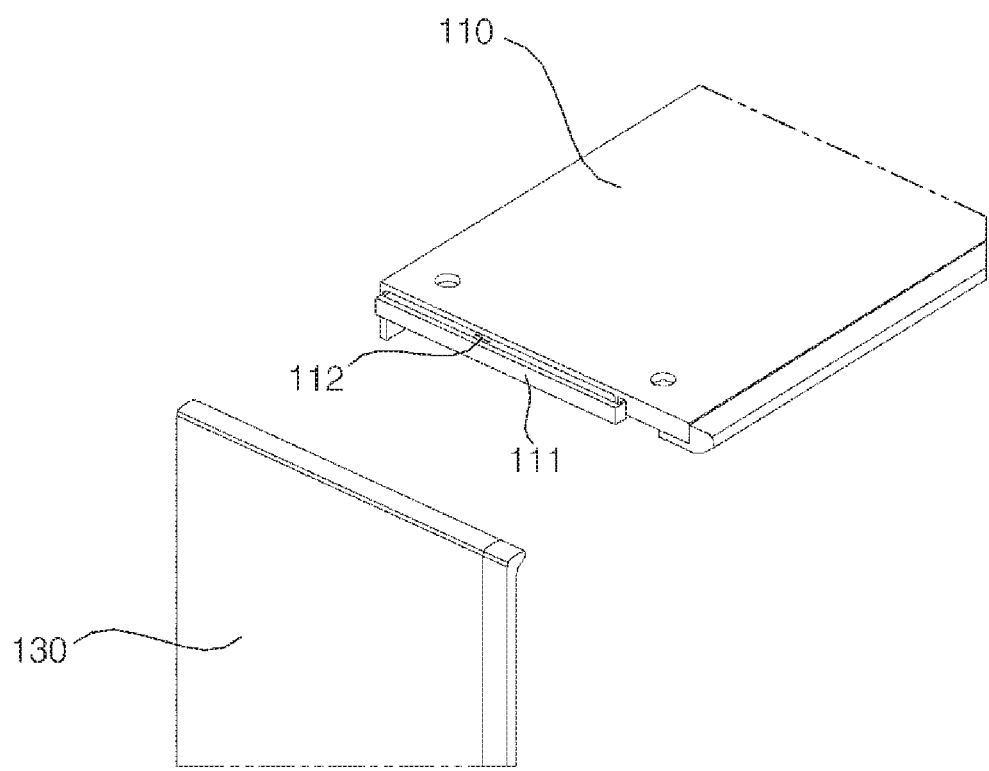
FIG. 10 is a left perspective view illustrating an upper panel and a left side panel shown in FIG. 4.
Figure 11:
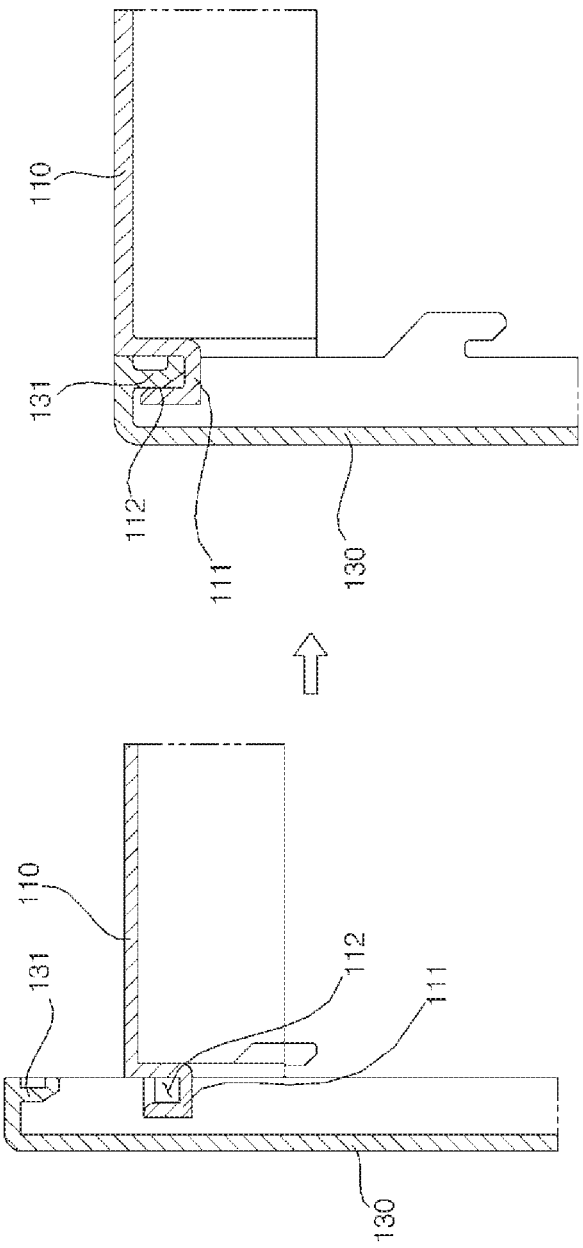
FIG. 11 is a sectional view illustrating a process of coupling the upper panel with the left side panel shown in FIG. 9 and FIG. 10.

Hereinafter, a process of manufacturing the cabinet 100 will be described with reference to FIG. 9 to FIG. 12. FIG. 9 is a right perspective view illustrating an upper panel and a left side panel shown in FIG. 4, FIG. 10 is a left perspective view illustrating an upper panel and a left side panel shown in FIG. 4, FIG. 11 is a sectional view illustrating a process of coupling the upper panel with the left side panel shown in FIG. 9 and FIG. 10, and FIG. 12 is a rear perspective view illustrating a lower panel and a left side panel shown in FIG. 4.

Referring to FIG. 9 to FIG. 12, first end ribs 111 having first end grooves 112 at top sides thereof may be formed at both ends of the upper panel 110, respectively. The first end ribs 111 may protrude to both end sides of the upper panel to have a square shape. The first end groove 112 may have the same square shape as that of the first end rib 111. Although FIG. 9 to FIG. 12 show only the first end rib 111 formed at a left end of the upper panel 110, the same first end rib 111 as the first end rib 111 formed at a left end of the upper panel 110 may be formed at the right end of the upper panel 110.

Moreover, second end ribs 131 inserted into the first end grooves 112 may be formed at an inner side of the left side panel 130 and an inner side of the right side panel 140, respectively. The second end rib 131 may protrude from an inner top side of the left side panel 130 downward to have a square shape. Although FIG. 9 to FIG. 12 show only the second end rib 131 formed at a top end of the left side panel 130, the same second end rib 131 as the second end rib 131 formed at the top end of the left side panel 130 may be formed at a top end of the right side panel 140. The second end rib 131 may slide the left side panel 130 and the right side panel 140 to be inserted into the first end groove 112 at a top side of the first end rib 111, to couple a top end of the left side panel 130 with a left end of the upper panel 110, and to couple a top end of the right side panel 140 with a right end of the upper panel 110.

Further, third end ribs 123 having second end grooves 122 at top sides thereof may be formed at both top ends of the lower panel 120, respectively. A pair of third end ribs 123 may have a circular shape and may be spaced apart from each other forward and rearward at both ends of the lower panel 120. The second end groove 122 may have the same circular shape as that of the third end rib 123. Although FIG. 9 to FIG. 12 show only the third end rib 123 formed at a left top side of the lower panel 120, the same third end rib 123 as the third end rib 123 formed at a left top side of the lower panel 120 may be formed at the right top side of the lower panel 120.

Furthermore, fourth end ribs 134 inserted into the second end grooves 122 may be formed at an inner side of the left side panel 130 and an inner side of the right side panel 140. The fourth end rib 134 may protrude in a direction perpendicular to an inner side of the left side panel 130 and an inner side of the right side panel 140 and an end of the fourth end rib 134 may have a shape bent downward at 90° and may be inserted into the second end groove 122. Although FIG. 9 to FIG. 12 show only the fourth end rib 134 formed at a bottom end of the left side panel 130, the same fourth end rib 134 as the fourth end rib 134 formed at a bottom end of the left side panel 130 may be formed at a bottom end of the right side panel 140. The fourth end rib 134 may slide the left side panel 130 and the right side panel 140 to be inserted into the second end groove 122 at a top side of the third end rib 123, to couple a bottom end of the left side panel 130 with a left end of the upper panel 120, and to couple a bottom end of the right side panel 140 with a right end of the lower panel 120.

As described above, since the left side panel 130 and the right side panel 140 may be coupled to the upper panel 110 and the lower panel 120 in a upward and downward sliding scheme, various function modules 300, 400, 500, 600, 700, 800, and 810 installed inside the frame 200 may fail. When the bathroom management apparatus is installed on a bathroom wall, the left side panel 130 and the right side panel 140 may slide upward to be separated, and the function modules 300, 400, 500, 600, 700, 800, and 810 may be easily separated from the frame 200 to be repaired.

Referring to FIG. 12, the lower panel 120 may further include a locking rib 124 which may be locked with a third locking boss 163 formed at a control panel 160 through a screw. That is, the third locking boss 163 may be locked with the locking rib 124 through the screw so that the control panel 160 is coupled with the lower panel 120.

Figure 13:
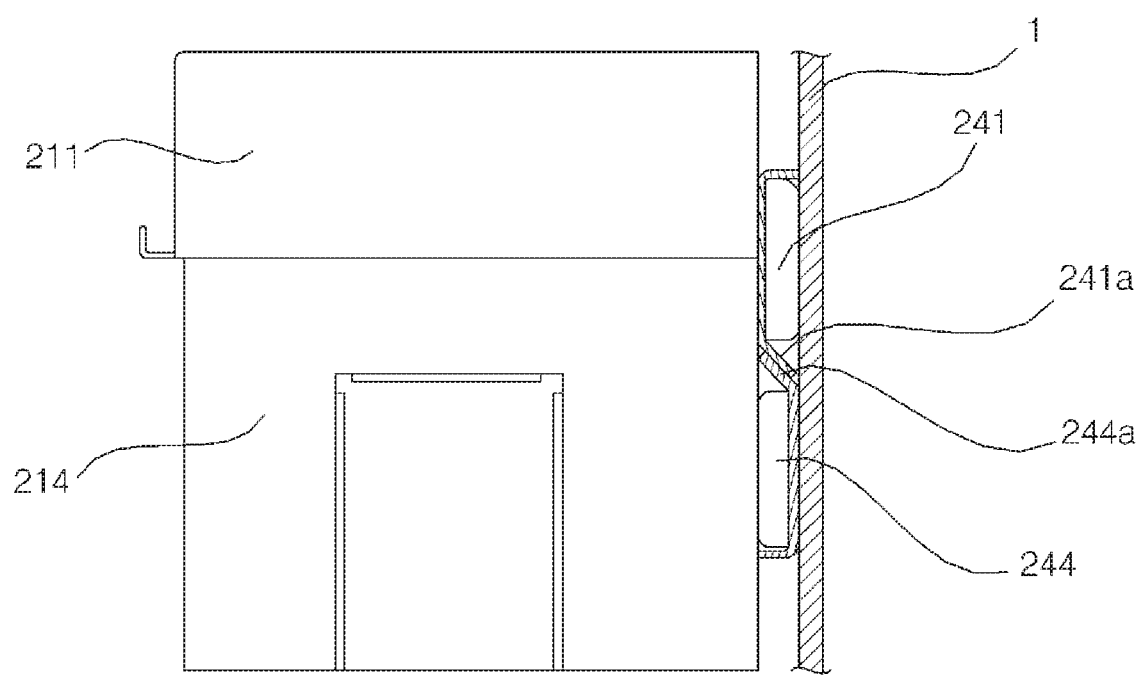
FIG. 13 is a side sectional view illustrating a state that the bathroom management apparatus according to an embodiment is installed on a bathroom wall.
Figure 14:
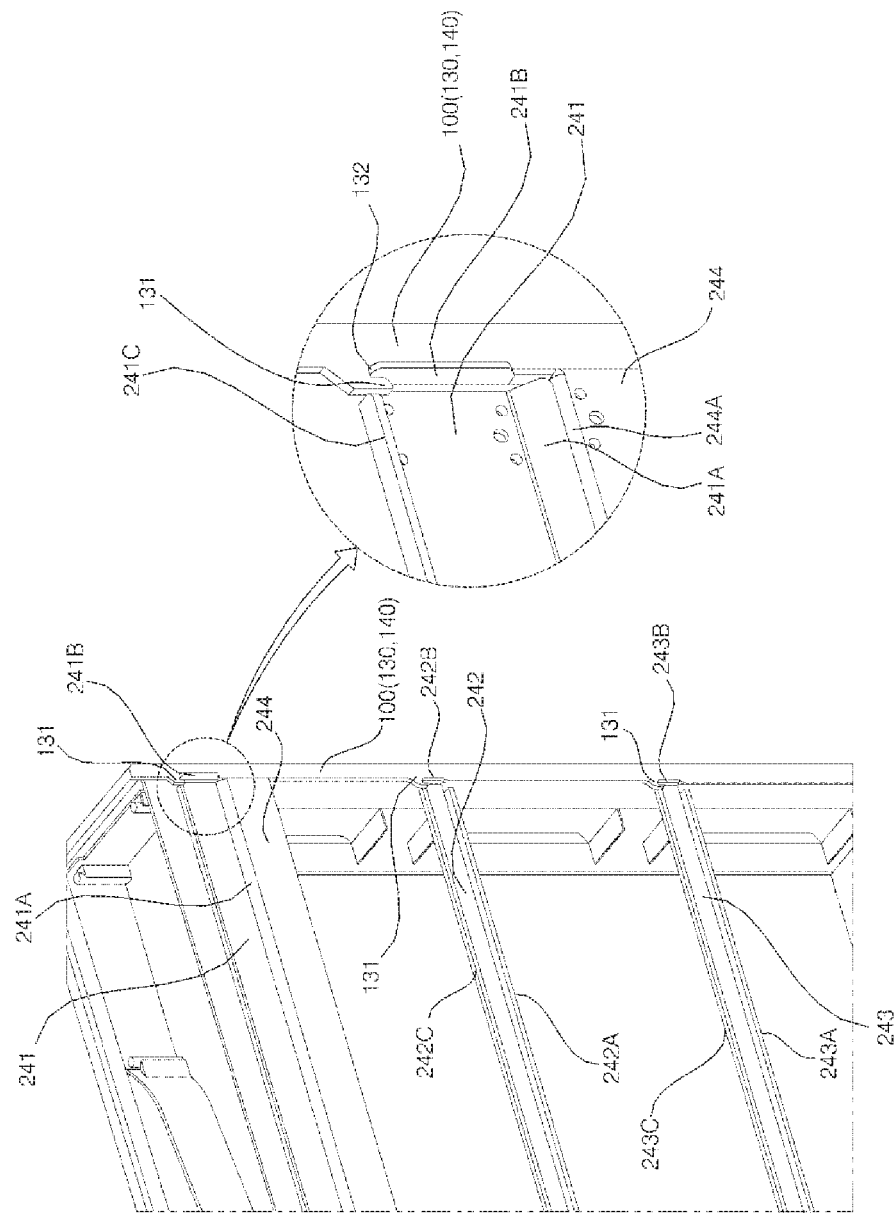
FIG. 14 is a partially rear perspective view of FIG. 3.

FIG. 13 is a side sectional view illustrating a state that the bathroom management apparatus is installed on a bathroom wall, and FIG. 14 is a partially rear perspective view of FIG. 3. Referring to FIG. 13 and FIG. 14, a back bracket 240 may be longitudinally formed horizontally. The back bracket may be coupled with the left side frame 213 and the right side frame 214 of the first frame body 210 and the left side frame 213 and the right side frame 214 of the second frame body 220 to connect the first frame body 210 with the second frame body 220. A left end of the back bracket 240 may be coupled with a rear surface of the left side frame 213 of the first frame body 210, and a right end of the back bracket 240 may be coupled with a rear surface of the right side frame 214 of the first frame body 220. The back bracket 240 may include an upper back bracket 241 located at the upper most position of the frame 200 and lower back brackets 242 and 243 located below the upper back bracket 241. Two lower back brackets 242 and 243 may be spaced apart from each other vertically.

A length of the back bracket 240 may be determined according to a number of frame bodies 210 and 220. That is, when one of frame bodies 210 and 220 is provided, the back bracket 240 may be short. When two or more frame bodies 210 and 220 extend, the back bracket 240 may be longer.

A mounting bracket 244 for mounting the bathroom management apparatus to a wall may be provided at a wall of the bathroom. The mounting bracket 244 mat have the same structure as that of the upper back bracket 241 to support the upper back bracket 241. That is, a reverse positioning of the upper back bracket 214 may be used as a mounting bracket 244. A first inclined part or tab 244A may be inclined toward a top end of the mounting bracket 244 to protrude in a forward direction upward.

A second inclined part (or second inclined tab) 241A may be inclined toward a bottom end of the upper back bracket 241 to protrude in a rearward direction downward. When the mounting bracket 244 is installed on a bathroom wall 1, the second inclined tab 241A may be inserted into a space between the first inclined tab 244A and the bathroom wall 1 to be supported at the first inclined tab 244A so that the bath management apparatus may be installed on the bathroom wall 1.

Side bending parts or tabs 241B, 242B, and 243B may be formed at both ends of the upper back bracket 241 and the lower back brackets 242 and 243 to be bent rearward. Further, the left side panel 130 and the right side panel 140 of the cabinet 100 may include locking ribs 131 having grooves 132 in which the side bending tabs 241B, 242B, and 243B are inserted, respectively. The locking ribs 131 may protrude to lateral surfaces of the left side panel 130 and the right side panel 140 from a rear surface of the left side panel 130 and the right side panel 140, respectively.

The grooves 132 may be formed at bottom sides of the locking rib 131 so that top sides of the side bending tabs 241B, 242B, and 243B may be inserted into the grooves 132, respectively. The side bending tabs 241B, 242B, and 243B may be inserted into the grooves 132 formed in the locking ribs 131 so that the frame body 210 does not oscillate in rightward and leftward directions when the frame body 210 is installed inside the cabinet 100.

Furthermore, an upper bending part or tab 241C may be formed at a top end of the upper back bracket 241 to protrude rearward. The stiffness of the upper back bracket 241 may be improved due to the upper bending tab 241C, the side bending tab 241B, and the second inclined tab 241A.

Moreover, upper bending parts or tabs 242C and 243C may be formed at upper ends of the lower back brackets 242 and 243 to protrude rearward. Lower bending parts or tabs 242A and 243A may be formed at bottom ends of the lower back brackets 242 and 243 to protrude rearward. The stiffness of the lower back brackets 242 and 243 may be improved due to the lower bending tabs 242C and 243C, the lower bending parts 242A and 243A, and the side bending parts 242B and 243B.

Figure 15:
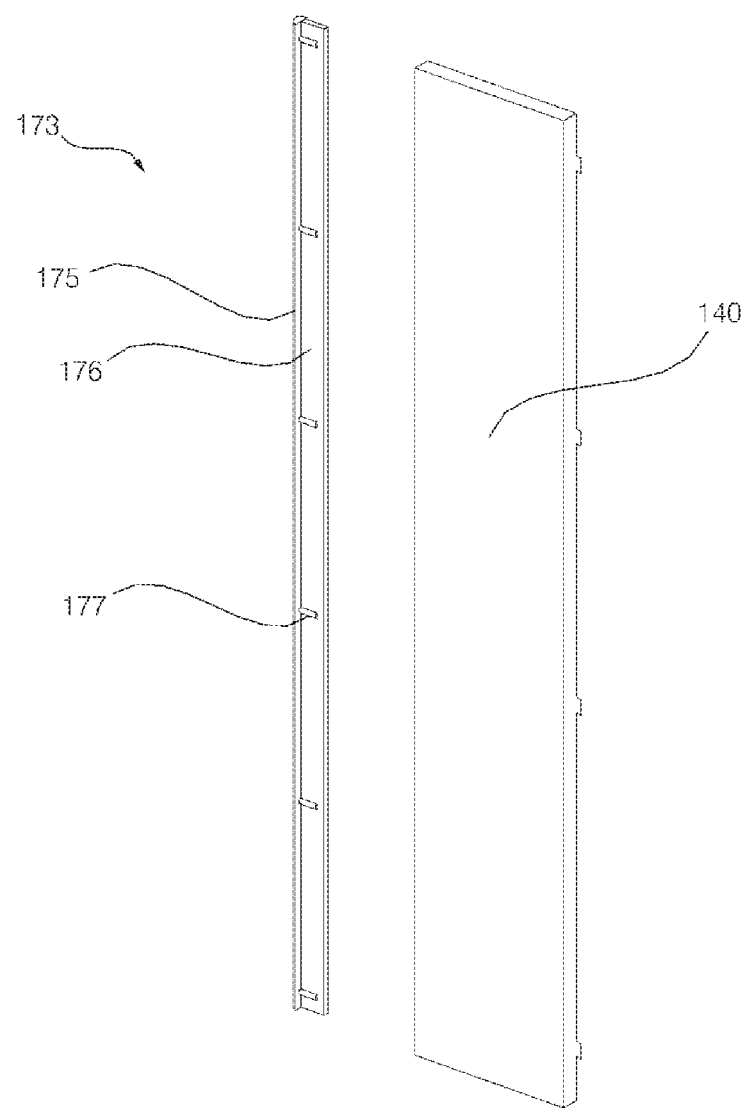
FIG. 15 is a left perspective view illustrating a right side panel and a decoration member shown in FIG. 4.

Hereinafter, an operation of coupling decoration members 171, 172, and 173 with the upper panel 110, the left side panel 130, and the right side panel 140 will be described with reference to FIG. 15 and FIG. 16. FIG. 15 is a left perspective view illustrating a right side panel and a decoration member shown in FIG. 4, and FIG. 16 is a right perspective view illustrating a right side panel and a decoration member shown in FIG. 4.

Referring to FIG. 15 and FIG. 16, the decoration members 171, 172, and 173 may include front surfaces 175 and lateral surfaces 176 protruding rearward of one side of the front surface 175. When the decoration members 171, 172, and 173 are installed at the upper panel 110, the left side panel 130, and the right side panel 140, the front surfaces 175 may be located at front ends of the left side panel 130 and the right side panel 140, respectively, and the lateral surfaces 176 may be located at inner sides of the left side panel 130 and the right side panel 140.

Locking protrusions 177 may protrude rearward from front surfaces of the decoration members 171, 172, and 173. Although FIG. 15 and FIG. 16 illustrate that the locking protrusion 177 is formed at only the front surface of the third decoration member 173, the same locking protrusions 177 as the locking protrusion may be formed at the front surface of the first decoration member 171 and the front surface of the second decoration member 172.

Further, first locking holes 147 in which the locking protrusion 177 is inserted and coupled, may be formed at a front end of the upper panel 110, a front end of the left side panel 130, and a front end of the right side panel 140. The locking protrusion 177 may be inserted and coupled in the first locking hole 147 so that the decoration members 171, 172, and 173 are coupled with the upper panel 110, the left side panel 130, and the right side panel 140, respectively. Although FIG. 15 and FIG. 16 illustrate that the locking hole 147 is formed in only the right side panel 140, the same first locking holes 147 as the first locking hole 147 may be formed at the upper panel 110 and the left side panel 130, respectively.

Referring to FIG. 16, second module locking protrusions 149 may be formed in the left side panel 130 and the right side panel 140, respectively. The second module locking protrusions 149 may protrude inward of front ends of the left side panel 130 and the right side panel 140 and may be inserted into a module locking groove 635 formed at the first module locking protrusion 630 shown in FIG. 8 to fix the function modules 300, 400, 500, 600, and 700. Although FIG. 15 and FIG. 16 illustrate that the second module locking protrusion 149 is formed at only a front end of the right side panel 140, the same second module locking protrusion 149 as the second module locking protrusion may be formed at the front end of the left side panel 130.

As shown in FIG. 9 to FIG. 12, since the left side panel 130 and the right side panel 130 may be coupled with the upper panel 110 and the lower panel 120 in a upward and downward sliding scheme, when the left side panel 130 and the right side panel 140 slide upward and downward, the module locking groove 635 may be formed at a top side of the first module locking protrusion 630 so that the second module locking protrusion 149 is inserted into the module locking groove 635 to be locked with the first module locking protrusion 630.

Figure 17:
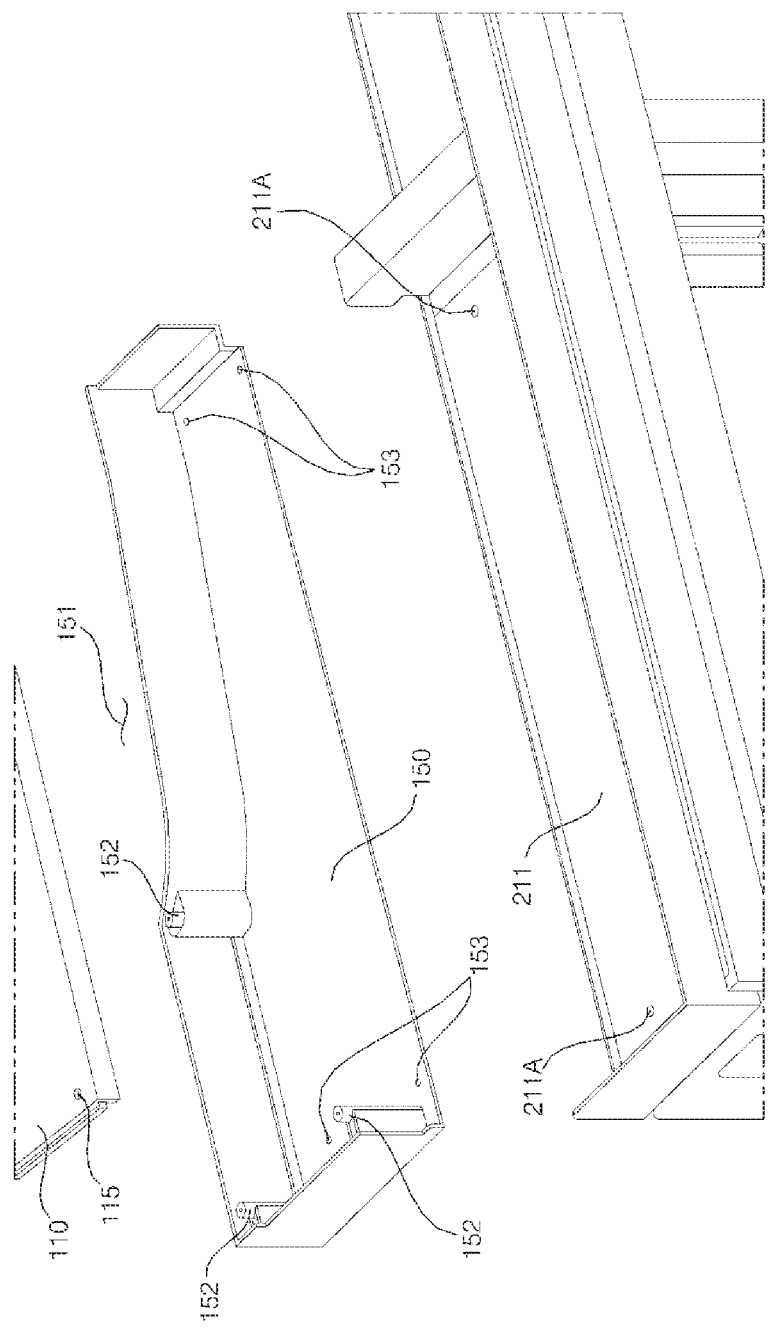
FIG. 17 is a view illustrating an upper panel, an upper cover, and an upper frame shown in FIG. 4.
Figure 18:
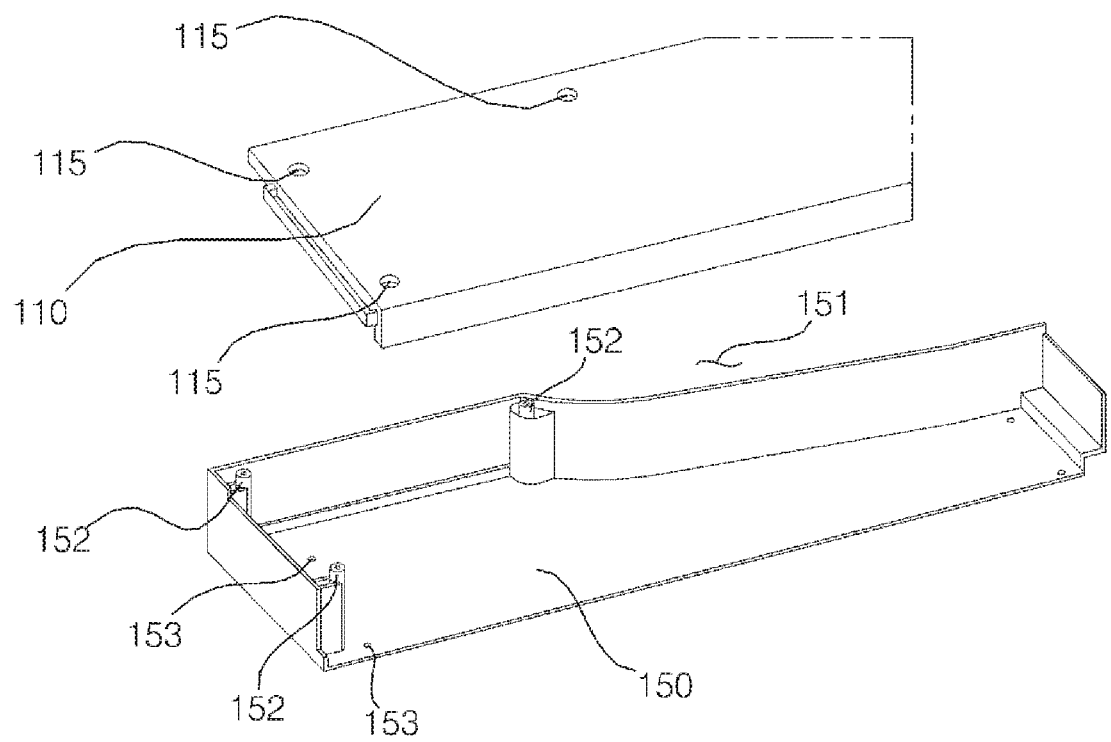
FIG. 18 is a view illustrating an upper panel and an upper cover shown in FIG. 4.

Hereinafter, an operation of coupling the upper cover 150 with the upper panel 110 and the upper frame 211 will be described with reference to FIG. 17 and FIG. 18. FIG. 17 is a view illustrating an upper panel, an upper cover, and an upper frame shown in FIG. 4, and FIG. 18 is a view illustrating an upper panel and an upper cover shown in FIG. 4. Referring to FIG. 17 and FIG. 18, the upper cover 150 may include a first locking boss 152 locked with the upper panel 110 and a second locking hole 153 locked with the upper frame 211.

Three total first locking bosses 152 may be provided. Two first locking bosses 152 may be spaced apart from each other forward and rearward at an inner side of a lateral surface distant from a concave groove 151 of both lateral surfaces of the upper cover 150, and one first locking boss 152 may be formed a region close to the concave groove 151 in a front surface of the upper cover 150.

The upper panel 110 may include a locking hole 115 locked with the first locking boss 152 with a screw. The number of locking holes 115 may be formed at a position corresponding to the first locking boss 152 by a corresponding number of the first locking bosses 152. A screw may be inserted into the locking hole 115 in a top side of the upper panel 110 to lock the screw with the locking boss 152 so that the upper cover 150 may be locked with an upper panel 110 of the cabinet 100.

Four total second locking bosses 153 may be provided. Two second locking bosses 153 may be spaced apart from each other forward and rearward at a left region of a bottom surface of the upper cover 150, and two second locking bosses 153 may be spaced apart from each other forward and rearward at a right region of the bottom surface of the upper cover 150.

The upper frame 211 may include a locking hole 211A locked with the second locking boss 153 with a screw. The number of locking holes 211A may be formed at a position corresponding to the second locking hole 153 by the corresponding number of the second locking hole 153. A screw may be inserted into the locking hole 211A in a top side of the upper cover 150 to lock the screw with the locking hole 211A so that the upper cover 150 is locked with an upper frame 211 of the frame 200.

Figure 19:
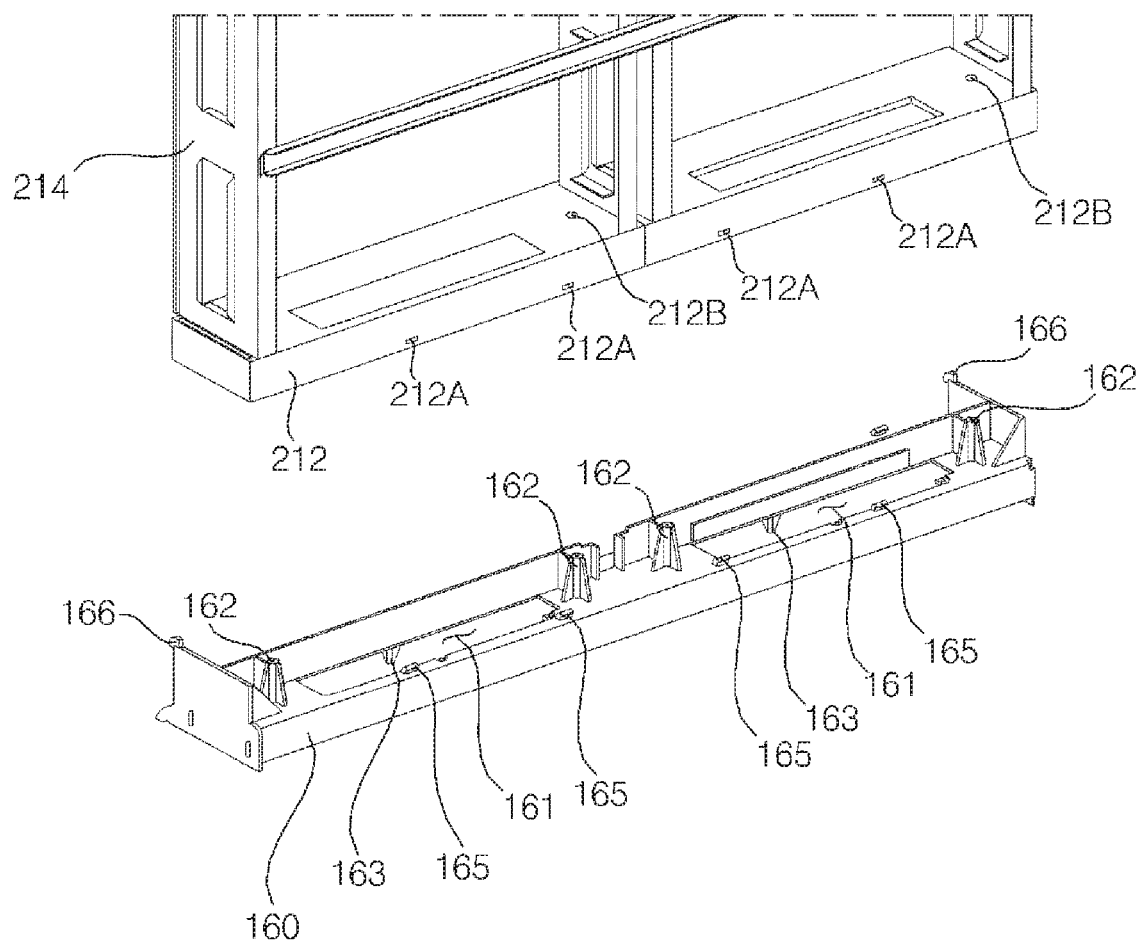
FIG. 19 is an exploded perspective view illustrating a lower panel and a control panel shown in FIG. 4.

Hereinafter, an operation of coupling the control panel 160 with the lower frame 212 and the lower panel 120 will be described with reference to FIG. 19 and FIG. 20. FIG. 19 is an exploded perspective view illustrating a lower panel and a control panel shown in FIG. 4, and FIG. 20 is a combined perspective view illustrating a lower panel and a control panel shown in FIG. 4.

Figure 20:
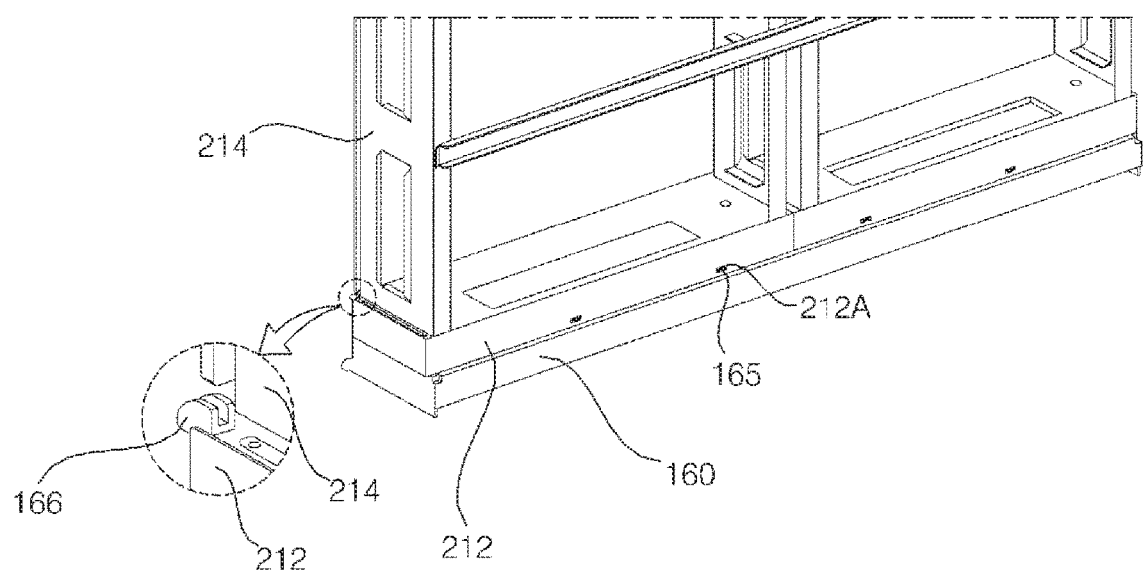
FIG. 20 is a combined perspective view illustrating a lower panel and a control panel shown in FIG. 4.

Referring to FIG. 12, FIG. 19, and FIG. 20, a hook hole 212A may be formed at a rear surface of the lower frame 212. A plurality of hook holes 212A may be spaced apart from each other rightward and leftward. Two hook holes 212A may be formed in one of frame bodies 210 and 220.

Further, the control panel 160 may include a first hook protrusion 165 inserted and locked in the hook hole 212A and a second hook protrusion 166 locked with a top end of the lower frame 212. The number of hook protrusions 165 may be formed at a position corresponding to the hook holes 212A by the corresponding number of the hook holes 212A. The hook protrusion 165 may protrude downward of a rear side of a top surface of the control panel 160. The second hook protrusion 166 may protrude rearward of a front end of both sides of the control panel 160. The control panel 160 may be moved rearward from a forward direction of the lower frame 212 to insert the first hook protrusion 165 into the hook hole 212A, and to lock the second hook protrusion 166 with a top end of the lower frame, so that the control panel 160 is optionally locked with a lower frame 212 of the frame 200.

The control panel 160 may further include a second locking boss 162 locked with the lower frame 212 of the frame 200 and a third locking boss 163 locked with a lower panel 120 of the cabinet 100. The second locking boss 162 may protrude upward from a top surface of the control panel 160, and the third locking boss 163 may protrude downward from a bottom surface of the control panel 160.

A plurality of second locking bosses 162 may be spaced apart from each other rightward and leftward. Two second locking bosses 162 may be formed in one of frame bodies 210 and 220. Further, the lower frame 211 may include a locking hole 211A locked with the second locking boss 153 with screw. The number of locking holes 212B may be formed at a position corresponding to the second locking boss 162 by the corresponding number of the second locking boss 162.

After the control panel 160 is optionally locked with the lower frame 212 using the first hook protrusion 165 and the second hook protrusion 166, a screw may be inserted into the locking hole 212B at a top side of the lower frame 212 and then the screw may be locked with the second locking boss 162, so that the control panel 160 is locked with a lower frame 212 of the frame 200. In addition, a locking rib 124 formed on a top surface of the lower panel 120 may be locked with a third locking boss 163 formed at a top surface of the control panel 160 by inserting the screw into a bottom side of the lower panel 120 of the cabinet 100 so that the control panel 160 is locked with a lower panel 120 of the cabinet 100.

As described above, when the function modules 300, 400, 500, 600, 700, and 810 are inserted into the frame 200, after the guide rib 610 is placed on a top side of the inner rib 215, if a user pushes the function module s 300, 400, 500, 600, 700, and 810, the function module s 300, 400, 500, 600, 700, and 810 may be inserted into a mounting space inside the frame 200 so that the function modules 300, 400, 500, 600, 700, and 810 may be freely added and disposed.

After a wire of the function modules 300, 400, 500, 600, 700, and 810 is discharged to an outer side of the frame 200 through a first opening portion 216, wiring may be possible through a path between a front outer rib 217 and a rear outer rib 217 so that wiring of the function module s 300, 400, 500, 600, 700, and 810 becomes easy.

Hereinafter, an installation position of function modules 300, 400, 500, 600, 700, and 810 by taking into consideration storage convenience and usability of a user will be described with reference to FIG. 5 and FIG. 21. FIG. 21 illustrates an installation position of a function module by taking into consideration storage convenience and usability of a user.

As described above, when two frame bodies 210 and 220 include a first frame body 210 and a second frame body 220, the frame 200 may provide a first mounting space S1, a second mounting space S2, a third mounting space S3, a fourth mounting space S4, a fifth mounting space S5, and a sixth mounting space S6. When the frame bodies 210 and 220 include only the first frame body 210, the frame 200 may provide only the first mounting space S1, the second mounting space S2, and the third mounting space S3. Since the various number of the function modules 300, 400, 500, 600, 700, and 810 may be selected by the user, optimal installation positions of function modules 300, 400, 500, 600, 700, and 810 by taking into consideration storage convenience and usability of a user will be described.

Referring to FIG. 5 and FIG. 21(a), when the frame bodies 210 and 220 include the first frame body 210 and the second frame body 220, a towel care module 300 may be mounted in at least one of the first mounting space S1, the second mounting space S2, the third mounting space S3, the fourth mounting space S4, the fifth mounting space S5, and the sixth mounting space S6. Since a towel may be used often in a bathroom, the towel care module 300 may be mounted in at least one of the first mounting space S1, the second mounting space S2, the third mounting space S3, the fourth mounting space S4, the fifth mounting space S5, and the sixth mounting space S6. If the frame bodies 210 and 220 include only the first frame body 210, the towel care module 300 may be mounted in at least one of the first mounting space S1, the second mounting space S2, and the third mounting space S3.

Referring to FIG. 5 and FIG. 21(b), when the frame bodies 210 and 220 include the first frame body 210 and the second frame body 220, a secret box module 500 may be mounted in the first mounting space S1 and the fourth mounting space S4. Since the secret box module 500 may be located at a position not to be exposed to outsiders or children as a place for storing secret products, the secret box module 500 may be located at the first mounting space S1 and the fourth mounting space S4 which are the upper most space among the first mounting space S1, the second mounting space S2, the third mounting space S3, the fourth mounting space S4, the fifth mounting space S5, and the sixth mounting space S6. If the frame bodies 210 and 220 include the first frame body 210, the secret box module 500 may be mounted in the first mounting space S1.

Referring to FIG. 5 and FIG. 21(c), when the frame bodies 210 and 220 include the first frame body 210 and the second frame body 220, a refrigeration module 600 may be mounted in the first mounting space S1, the second mounting space S2, the third mounting space S3, the fourth mounting space S4, the fifth mounting space S5, and the sixth mounting space S6. Since the refrigeration module 600 may store cosmetics and medical products to be used once or twice a day, the refrigeration module 600 may be mounted in the second mounting space S2, the third mounting space S3, and the fifth mounting space S5 being middle and lower spaces easy to use among the first mounting space S1, the second mounting space S2, the third mounting space S3, the fourth mounting space S4, the fifth mounting space S5, and the sixth mounting space S6. If the frame bodies 210 and 220 include only the first frame body 210, the refrigeration module 600 may be mounted in the second mounting space S2 and the third mounting space S3.

Referring to FIG. 5 and FIG. 21(d), when the frame bodies 210 and 220 include the first frame body 210 and the second frame body 220, a charging module 700 may be mounted in the first mounting space S1, the second mounting space S2, the third mounting space S3, the fourth mounting space S4, the fifth mounting space S5, and the sixth mounting space S6. Since the charging module 700 may store electronic products such as hair dryers or electric shavers or a charger to charge the electronic products to be used once or twice a day, charging module 700 may be mounted in the second mounting space S2, the third mounting space S3, and the fifth mounting space S5 being middle and lower spaces easy to use among the first mounting space S1, the second mounting space S2, the third mounting space S3, the fourth mounting space S4, the fifth mounting space S5, and the sixth mounting space S6. If the frame bodies 210 and 220 include only the first frame body 210, the charging module 700 may be mounted in the second mounting space S2 and the third mounting space S3.

Referring to FIG. 5 and FIG. 21(e), when the frame bodies 210 and 220 include the first frame body 210 and the second frame body 220, the sterilizing module 400 and the air conditioning module 810 may be mounted in the third mounting space S3 and the sixth mounting space S6. Since a first air outlet 2 may be formed at a front bottom portion of the cabinet 100, and a second air outlet 121 may be formed at a bottom surface of the cabinet 100, the air conditioning module 810 may be mounted in the third mounting space S3 and the sixth mounting space S6 being a lower space close to the first air outlet 2 and the second air outlet 121 among the first mounting space S1, the second mounting space S2, the third mounting space S3, the fourth mounting space S4, the fifth mounting space S5, and the sixth mounting space S6. Further, since the sterilizing module 400 and the air conditioning module 810 are integrally formed, the sterilizing module 400 may be mounted in the third mounting space S3 and the sixth mounting space S6 as in the air conditioning module 810.

Although the sterilizing module 400 and the air conditioning module 810 are not integrally formed, since the sterilizing module 400 may store a toothbrush to be used once to three times a day, the sterilizing module 400 may be mounted in the third mounting space S3 and the sixth mounting space S6 being a lower space easy to use among the first mounting space S1, the second mounting space S2, the third mounting space S3, the fourth mounting space S4, the fifth mounting space S5, and the sixth mounting space S6. If the frame bodies 210 and 220 include only the first frame body 210, the sterilizing module 400 and the air conditioning module 810 may be mounted in the third mounting space S3.

As described above, when the frame bodies 210 and 220 include the first frame body 210 and the second frame body 220, one of the towel care module 300 and the secret box module 500 may be installed at the first mounting space S1, one of the towel care module 300, the refrigeration module 600, and the charging module 700 may be installed at the second mounting space S2, one of the towel care module 300, the refrigeration module 600, the charging module 700, the sterilizing module 400 and the air conditioning module 810 may be installed at the third mounting space S3, one of the towel care module 300 and the secret box module 500 may be installed at the fourth mounting space S4, one of the towel care module 300, the refrigeration module 600, and the charging module 700 may be installed at the fifth mounting space S5, and one of the towel care module 300, the refrigeration module 600, the charging module 700, the sterilizing module 400 and the air conditioning module 810 may be installed at the sixth mounting space S6.

If the frame bodies 210 and 220 include only the first frame body 210, one of the towel care module 300 and the secret box module 500 may be installed in the third mounting space S3, one of the towel care module 300, the refrigeration module 600, and the charging module 700 may be installed at the second mounting space S2, and one of the towel care module 300, the refrigeration module 600, the charging module 700, the sterilizing module 400, and the air conditioning module 810 may be installed at the third mounting space S3.

As described above, when the frame bodies 210 and 220 include the first frame body 210 and the second frame body 220, the sterilizing module 400 and the air conditioning module 810 may be installed at the third mounting space S3 and the sixth mounting space S6. Accordingly, hereinafter, which one of the third mounting space S3 and the sixth mounting space S6 are the sterilizing module 400 and the air conditioning module 810 installed by taking into consideration a position of a washstand installed in the bathroom will be described with reference to FIG. 5 and FIG. 22.

Figure 22:
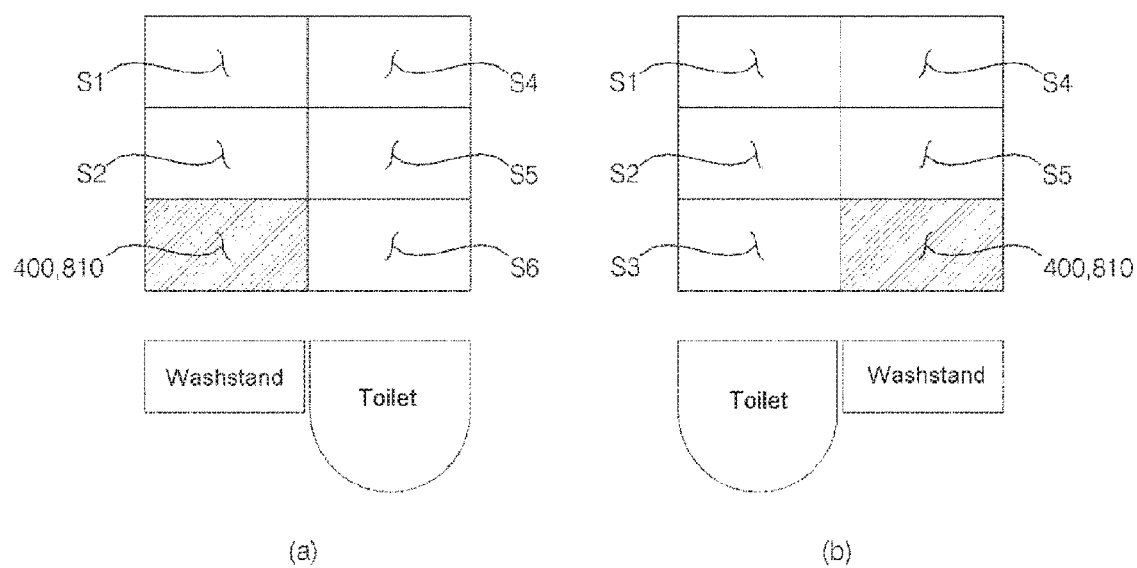
FIG. 22 illustrates installation positions of a sterilizing module and an air conditioning module by taking into a washstand installed in a bathroom.

FIG. 22 illustrates installation positions of a sterilizing module and an air conditioning module by taking into a washstand installed in a bathroom. Referring to FIG. 5 and FIG. 22, positions of a washstand and a toilet installed in the bathroom may be changed according to users. That is, in a bathroom of a user, a washstand may be located at a left side of a toilet, or the washstand may be located at a right side of the toilet.

The bathroom management apparatus according to an embodiment may be configured so that a user's body may be dried by discharging air blown from the air conditioning module 810 through the first air outlet 2, and an inside of the bathroom may be dried by discharging the air blown from the air conditioning module 810 through the second air outlet 121. Since a shower may be connected to the washstand, the user may shower in front of the washstand to dry a user's body using air discharged through the first air outlet 2. Further, since the washstand may be the most frequently used device among devices inside the bathroom, the washstand may need to be dried quickly. Accordingly, the air conditioning module 810 may be installed at a space close to the washstand between the third mounting space S3 and the sixth mounting space S6.

That is, as shown in FIG. 22(a), when the washstand is installed at a left side of a toilet, the sterilizing module 400 and the air conditioning module 810 may be installed at the third mounting space S3 to be disposed on the washstand. As shown in FIG. 22(b), when the washstand is installed at a right side of a toilet, the sterilizing module 400 and the air conditioning module 810 may be installed at the sixth mounting space S6 to be disposed on the washstand.

As described above, in the bathroom management apparatus, installation positions of function modules 300, 400, 500, 600, 700, and 810 may be optimized by taking into consideration storage convenience and usability of a user. Further, when the function modules 300, 400, 500, 600, 700, and 810 are inserted into the frame 200, after the guide rib 610 is placed on a top side of the inner rib 215, if a user pushes the function modules 300, 400, 500, 600, 700, and 810, the function modules 300, 400, 500, 600, 700, and 810 may be inserted into a mounting space inside the frame 200 so that the function modules 300, 400, 500, 600, 700, and 810 may be freely added and detached.

A bathroom management apparatus may include a cabinet of which a front surface is open; a frame installed in the cabinet to reinforce stiffness of the cabinet; and a function module including at least one of a towel care module, a sterilizing module, a secret box module, a refrigerating module, a charging module, and an air conditioning module and installed in the frame, wherein the frame provides a first mounting space, a second mounting space at a lower side of the first mounting space, and a third mounting space at a lower side of the second mounting space therein, one of the towel care module and the secret box module is installed at the first mounting space, one of the towel care module, the refrigerating module, and the charging module is installed at the second mounting space, and one of the towel care module, the sterilizing module, the refrigerating module, the charging module, and the air conditioning module is installed at the third mounting space. Guide ribs may be formed at both sides of the function module, respectively, and inner ribs may be formed at both side frames of the frames to guide and support the guide ribs when inserting the function module into the frame.

According to a first objective, an installation position of a function module may be optimized by taking into consideration storage convenience and usability of a user. According to a second objective, when the function module is inserted into the frame, after the guide rib is placed on a top side of the inner rib, if a user pushes the function module, the function module may be inserted into a mounting space inside the frame so that the function module may be freely added or detached.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bathroom management apparatus comprising:
   a cabinet having an open front surface;
   at least one frame configured to be attached to the cabinet to reinforce stiffness of the cabinet, the at least one frame including a left side frame and a right side frame; and
   at least one function module box configured to be attached to the frame, and forming a space therein, wherein the at least one frame includes a plurality of mounting spaces arranged in a vertical direction,
   wherein module locking ribs are formed at both sides of the at least one function module box to be locked with front ends of each of the left and right side frames, respectively, wherein at least one first module locking protrusion having a module locking groove is formed in the module locking rib, and second module locking protrusions are formed at left and right side panels of the cabinet and are inserted into respective module locking grooves to be locked with the at least one first module locking protrusion.

2. The bathroom management apparatus of claim 1, wherein guide ribs are formed at both sides of the at least one function module box, respectively, and inner ribs are formed at the left side frame and the right side frame of the at least one frame to guide and support the guide ribs when the at least one function module box is inserted into the at least one frame.

3. The bathroom management apparatus of claim 2, wherein first slots are formed in the left and right side frames, respectively, and the inner ribs protrude inward from a top side and a bottom side of each of the first slots.

4. The bathroom management apparatus of claim 3, wherein outer ribs protrude outward from a front side and a rear side of each of the first slots in outer sides of the left and right side frames, respectively.

5. The bathroom management apparatus of claim 1, wherein an upper frame of the at least one frame is spaced apart from an upper panel of the cabinet, and a lower frame of the at least one frame is spaced apart from a lower panel of the cabinet, and wherein the bathroom management apparatus further includes:
   an upper cover provided between the upper panel and the upper frame, coupled with the upper panel and the upper frame, and configured to cover a space between the upper panel and the upper frame, and
   a control panel provided between the lower panel and the lower frame, coupled with the lower panel and the lower frame.

6. The bathroom management apparatus of claim 5, wherein the cabinet includes a first air outlet spaced apart from the lower frame, and a second air outlet formed in the lower panel, and the function module box includes a heating device for blowing heated air, and an exhauster provided inside the control panel to switch air blown from the heating device to one of the first air outlet and the second air outlet.

7. The bathroom management apparatus of claim 5, further including:
   a door configured to open the open front surface of the cabinet; and
   a hinge provided at a rear top side of the door to be coupled with the upper frame, wherein a concave groove in which the hinge is received when the door is closed is formed at a front surface of the upper cover.

8. The bathroom management apparatus of claim 5, wherein the upper frame and the lower frame of the at least one frame each include cut lines configured to be punched out to form second slots,
   a third slot is formed beneath the second slot in the control panel, and
   a fourth slot is formed beneath the third slot of the lower panel of the cabinet.

* * * * *